United States Patent
Sui et al.

(10) Patent No.: US 12,421,307 B2
(45) Date of Patent: Sep. 23, 2025

(54) ANTI-FGF19 ANTIBODIES

(71) Applicant: HUAHUI HEALTH LTD., Beijing (CN)

(72) Inventors: Jianhua Sui, Beijing (CN); Huisi Liu, Beijing (CN)

(73) Assignee: HUAHUI HEALTH LTD., Beijing (CN)

( * ) Notice: Subject to any disclaimer, the term of this patent is extended or adjusted under 35 U.S.C. 154(b) by 1023 days.

(21) Appl. No.: 17/427,301

(22) PCT Filed: Feb. 2, 2020

(86) PCT No.: PCT/CN2020/074154
§ 371 (c)(1),
(2) Date: Jul. 30, 2021

(87) PCT Pub. No.: WO2020/156539
PCT Pub. Date: Jun. 8, 2020

(65) Prior Publication Data
US 2022/0041706 A1    Feb. 10, 2022

(30) Foreign Application Priority Data
Feb. 2, 2019 (WO) ................ PCT/CN2019/074530

(51) Int. Cl.
*C07K 16/22* (2006.01)
*A61P 35/00* (2006.01)
*A61K 39/00* (2006.01)

(52) U.S. Cl.
CPC .............. *C07K 16/22* (2013.01); *A61P 35/00* (2018.01); *A61K 2039/505* (2013.01); *C07K 2317/33* (2013.01); *C07K 2317/565* (2013.01); *C07K 2317/73* (2013.01); *C07K 2317/76* (2013.01); *C07K 2317/92* (2013.01)

(58) Field of Classification Search
CPC ............. C07K 16/22; C07K 2317/33; C07K 2317/565; C07K 2317/73; C07K 2317/76; C07K 2317/92; C07K 2317/21; C07K 2317/34; C07K 2317/515; C07K 2317/56; A61P 35/00; A61K 2039/505
See application file for complete search history.

(56) References Cited

FOREIGN PATENT DOCUMENTS

| WO | WO2007136893 | 11/2007 | |
| WO | WO-2007136893 A2 * | 11/2007 | ............. C07K 16/22 |
| WO | WO2009035786 | 3/2009 | |

OTHER PUBLICATIONS

Turner et al., "Fibroblast growth factor signalling: from development to cancer", Nat. Rev. Cancer, 10, 116-129 (2010).
Xie et al., "FGF-19, A Novel Fibroblast Growth Factor with Unique Specificity for Fgfr4", Cytokine, 11, 729-735 (1999).
Holt et al., "Definition of a novel growth factor-dependent signal cascade for the suppression of bile acid biosynthesis", Genes & Develop., 17, 1581-1591 (2003).
Kurosu et al., "Tissue-specific Expression of βKlotho and Fibroblast Growth Factor (FGF) Receptor Isoforms Determines Metabolic Activity of FGF19 and FGF21", J Biol. Chem., 282, 26687-26695 (2007).
Lin et al., "Liver-specific Activities of FGF19 Require Klotho beta", J Biol. Chem., 282, 27277-27284 (2007).
Sawey et al., "Identification of a Therapeutic Strategy Targeting Amplified FGF19 in Liver Cancer by Oncogenomic Screening", Cancer Cell, 19, 347-358 (2011).
Wang et al., "Genomic Landscape of Copy Number Aberrations Enables the Identification of Oncogenic Drivers in Hepatocellular Carcinoma", Hepatology, 58: 706-717 (2013).
Ahn et al., "Genomic Portrait of Resectable Hepatocellular Carcinomas: Implications of RB1 and FGF19 Aberrations for Patient Stratification", Hepatology, 60, 1972-1982 (2014).
Schulze et al., "Exome sequencing of hepatocellular carcinomas identifies new mutational signatures and potential therapeutic targets", Nat Genet., 47, 505-511 (2015).
Desnoyers et al., "Targeting FGF19 inhibits tumor growth in colon cancer xenograft and FGF19 transgenic hepatocellular carcinoma models", Oncogene, 27, 85-97 (2008).
Li et al., "Up-regulation of fibroblast growth factor 19 and its receptor associates with progression from fatty liver to hepatocellular carcinoma", Oncotarget, 7, 52329-52339 (2016).
Llovet et al., "Hepatocellular carcinoma", Nat Rev Dis Primers, 2, 16018 (2016).
Bray et al., "Global Cancer Statistics 2018: Globocan Estimates of Incidence and Mortality Worldwide for 36 Cancers in 185 Countries", CA Cancer J Clin, 68, 394-424 (2018).
Miura et al., "Fibroblast growth factor 19 expression correlates with tumor progression and poorer prognosis of hepatocellular carcinoma", BMC Cancer, 12, 56 (2012).
Hyeon et al., "Expression of Fibroblast Growth Factor 19 Is Associated with Recurrence and Poor Prognosis of Hepatocellular Carcinoma", Dig. Dis. Sci., 58, 1916-1922 (2013).
Nicholes et al., "A Mouse Model of Hepatocellular Carcinoma Ectopic Expression of Fibroblast Growth Factor 19 in Skeletal Muscle of Transgenic Mice", Am J Pathol, 160, 2295-2307 (2002).
French et al., "Targeting FGFR4 Inhibits Hepatocellular Carcinoma in Preclinical Mouse Models", PLOS One, 7, e36713 (2012).
Hagel et al., "First Selective Small Molecule Inhibitor of FGFR4 for the Treatment of Hepatocellular Carcinomas with an Activated FGFR4 Signaling Pathway", Cancer Discov., 5, 424-437 (2015).
Kim et al., "First-in-human study of BLU-554, a potent, highly-selective FGFR4 inhibitor designed for hepatocellular carcinoma (HCC) with FGFR4 pathway activation", Eur J Cancer, 69, S41 (2016).

(Continued)

Primary Examiner — Samira J Jean-Louis
Assistant Examiner — Alyssa Rae Stonebraker
(74) Attorney, Agent, or Firm — FINNEGAN, HENDERSON, FARABOW, GARRETT & DUNNER LLP

(57) ABSTRACT

Provided are anti-FGF19 antibodies that selectively target N-terminus of fibroblast growth factor 19 (FGF19) and antigen-binding fragments thereof, as well as uses of said antibodies in treating a disease or disorder caused by or related to abnormal FGF19-FGFR4 signaling, e.g., cancer.

16 Claims, 13 Drawing Sheets

Specification includes a Sequence Listing.

(56) References Cited

OTHER PUBLICATIONS

Chan et al., "Abstract CT106: Ph I/II study of FGF401 in adult pts with HCC or solid tumors characterized by FGFR4/KLB expression", *Cancer Res.*, 77, CT106-CT106 (2017).

Joshi et al., "H3B-6527 Is a Potent and Selective Inhibitor of FGFR4 in FGF19-Driven Hepatocellular Carcinoma", *Cancer Res.*, 77, 6999-7013 (2017).

Ruggeri et al., "Abstract 1234: The novel FGFR4-selective inhibitor INCB062079 is efficacious in models of hepatocellular carcinoma harboring FGF19 amplification", *Cancer Res.*, 77, 1234-1234 (2017).

Pai et al., "Antibody-Mediated Inhibition of Fibroblast Growth Factor 19 Results in Increased Bile Acids Synthesis and Ileal Malabsorption of Bile Acids in Cynomolgus Monkeys", *Toxicological Sciences*, 126, 446-456 (2012).

Beenken et al, "The FGF family: biology, pathophysiology and therapy", *Nat Rev Drug Discov*, 8, 235-253 (2009).

Itoh et al., "Fibroblast growth factors: from molecular evolution to roles in development, metabolism and disease", *J Biochem*, 149, 121-130 (2011).

Goetz et al, "Exploring mechanisms of FGF signalling through the lens of structural biology", *Nat Rev Mol Cell Biol*, 14, 166-180 (2013).

International Search Report for PCT/CN2020/074154, dated May 20, 2021.

\* cited by examiner

US 12,421,307 B2

SEQUENCE LISTING

```
<160> NUMBER OF SEQ ID NOS: 24

<210> SEQ ID NO 1
<211> LENGTH: 216
<212> TYPE: PRT
<213> ORGANISM: Homo sapiens

<400> SEQUENCE: 1

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
                35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80
```

```
Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
    130                 135                 140

Leu Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
                180                 185                 190

Glu Thr Asp Ser Met Asp Pro Phe Gly Leu Val Thr Gly Leu Glu Ala
                195                 200                 205

Val Arg Ser Pro Ser Phe Glu Lys
    210                 215

<210> SEQ ID NO 2
<211> LENGTH: 8
<212> TYPE: PRT
<213> ORGANISM: Homo sapiens

<400> SEQUENCE: 2

Trp Gly Asp Pro Ile Arg Leu Arg
1               5

<210> SEQ ID NO 3
<211> LENGTH: 5
<212> TYPE: PRT
<213> ORGANISM: Artificial Sequence
<220> FEATURE:
<223> OTHER INFORMATION: 31A3 HCDR1

<400> SEQUENCE: 3

Ser Tyr Ala Met Ser
1               5

<210> SEQ ID NO 4
<211> LENGTH: 17
<212> TYPE: PRT
<213> ORGANISM: Artificial Sequence
<220> FEATURE:
<223> OTHER INFORMATION: 31A3 HCDR2

<400> SEQUENCE: 4

Ala Ile Ser Gly Ser Gly Gly Ser Thr Tyr Tyr Ala Asp Ser Val Lys
1               5                   10                  15

Gly

<210> SEQ ID NO 5
<211> LENGTH: 10
<212> TYPE: PRT
<213> ORGANISM: Artificial Sequence
<220> FEATURE:
<223> OTHER INFORMATION: 31A3 HCDR3

<400> SEQUENCE: 5

Asp Val Trp Gln Glu Leu Leu Phe Asp Tyr
1               5                   10
```

```
<210> SEQ ID NO 6
<211> LENGTH: 14
<212> TYPE: PRT
<213> ORGANISM: Artificial Sequence
<220> FEATURE:
<223> OTHER INFORMATION: 31A3 LCDR1

<400> SEQUENCE: 6

Thr Gly Thr Ser Ser Asp Val Gly Gly Tyr Asn Tyr Val Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: 31A3 LCDR2

<400> SEQUENCE: 7

Asp Val Ser Asn Arg Pro Ser
1               5

<210> SEQ ID NO 8
<211> LENGTH: 10
<212> TYPE: PRT
<213> ORGANISM: Artificial Sequence
<220> FEATURE:
<223> OTHER INFORMATION: 31A3 LCDR3

<400> SEQUENCE: 8

Ser Ser Tyr Thr Arg Ser Ser Thr Leu Val
1               5                   10

<210> SEQ ID NO 9
<211> LENGTH: 119
<212> TYPE: PRT
<213> ORGANISM: Artificial Sequence
<220> FEATURE:
<223> OTHER INFORMATION: 31A3 VH

<400> SEQUENCE: 9

Glu Val Gln Leu Leu Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Trp Gln Glu Leu Leu Phe Asp Tyr Trp Gly Gln Gly
            100                 105                 110

Thr Leu Val Thr Val Ser Ser
        115

<210> SEQ ID NO 10
<211> LENGTH: 110
<212> TYPE: PRT
<213> ORGANISM: Artificial Sequence
```

<220> FEATURE:
<223> OTHER INFORMATION: 31A3 VL

<400> SEQUENCE: 10

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Thr Arg Ser
                85                  90                  95

Ser Thr Leu Val Phe Gly Gly Gly Thr Gln Leu Thr Val Leu
            100                 105                 110

<210> SEQ ID NO 11
<211> LENGTH: 449
<212> TYPE: PRT
<213> ORGANISM: Artificial Sequence
<220> FEATURE:
<223> OTHER INFORMATION: 31A3 heavy chain

<400> SEQUENCE: 11

Glu Val Gln Leu Leu Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Trp Gln Glu Leu Leu Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Ala Pro Glu Leu Leu Gly Gly Pro
    210                 215                 220

Ser Val Phe Leu Phe Pro Pro Lys Pro Lys Asp Thr Leu Met Ile Ser

```
            225                 230                 235                 240
    Arg Thr Pro Glu Val Thr Cys Val Val Asp Val Ser His Glu Asp
                    245                 250                 255

Pro Glu Val Lys Phe Asn Trp Tyr Val Asp Gly Val Glu Val His Asn
                    260                 265                 270

Ala Lys Thr Lys Pro Arg Glu Glu Gln Tyr Asn Ser Thr Tyr Arg Val
                    275                 280                 285

Val Ser Val Leu Thr Val Leu His Gln Asp Trp Leu Asn Gly Lys Glu
            290                 295                 300

Tyr Lys Cys Lys Val Ser Asn Lys Ala Leu Pro Ala Pro Ile Glu Lys
    305                 310                 315                 320

Thr Ile Ser Lys Ala Lys Ala Glu Pro Lys Ser Cys Asp Lys Thr His
                    325                 330                 335

Thr Cys Pro Pro Cys Pro Gly Gln Pro Arg Glu Pro Gln Val Tyr Thr
                    340                 345                 350

Leu Pro Pro Ser Arg Asp Glu Leu Thr Lys Asn Gln Val Ser Leu Thr
                    355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
    385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
                    435                 440                 445

Lys

<210> SEQ ID NO 12
<211> LENGTH: 216
<212> TYPE: PRT
<213> ORGANISM: Artificial Sequence
<220> FEATURE:
<223> OTHER INFORMATION: 31A3 light chain

<400> SEQUENCE: 12

Gln Ala Gly Leu Thr Gln Pro Ala Ser Val Ser Gly Ser Pro Gly Gln
    1               5                   10                  15

Ser Ile Thr Ile Ser Cys Thr Gly Thr Ser Ser Asp Val Gly Gly Tyr
                    20                  25                  30

Asn Tyr Val Ser Trp Tyr Gln Gln His Pro Gly Lys Ala Pro Lys Leu
                    35                  40                  45

Met Ile Tyr Asp Val Ser Asn Arg Pro Ser Gly Val Ser Asp Arg Phe
            50                  55                  60

Ser Gly Ser Lys Ser Gly Asn Thr Ala Ser Leu Thr Ile Ser Gly Leu
    65                  70                  75                  80

Gln Thr Glu Asp Glu Ala Asp Tyr Tyr Cys Ser Ser Tyr Thr Arg Ser
                    85                  90                  95

Ser Thr Leu Val Phe Gly Gly Gly Thr Gln Leu Thr Val Leu Gly Gln
                    100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140
```

Pro Gly Ala Val Thr Val Ala Trp Lys Ala Asp Gly Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 13
<211> LENGTH: 10
<212> TYPE: PRT
<213> ORGANISM: Artificial Sequence
<220> FEATURE:
<223> OTHER INFORMATION: G1A8 HCDR3

<400> SEQUENCE: 13

Asp Asn Trp Gln Glu Leu Leu Phe Asp Tyr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: G1A8 LCDR3

<400> SEQUENCE: 14

Ser Ser Trp Thr Arg Ser Ser Gly Leu Val
1               5                   10

<210> SEQ ID NO 15
<211> LENGTH: 119
<212> TYPE: PRT
<213> ORGANISM: Artificial Sequence
<220> FEATURE:
<223> OTHER INFORMATION: G1A8 VH

<400> SEQUENCE: 15

Glu Val Gln Leu Leu Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Trp Gln Glu Leu Leu Phe Asp Tyr Trp Gly Gln Gly
            100                 105                 110

Thr Leu Val Thr Val Ser Ser
        115

<210> SEQ ID NO 16
<211> LENGTH: 110

```
<212> TYPE: PRT
<213> ORGANISM: Artificial Sequence
<220> FEATURE:
<223> OTHER INFORMATION: G1A8 VL

<400> SEQUENCE: 16

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Trp Thr Arg Ser
                85                  90                  95

Ser Gly Leu Val Phe Gly Gly Gly Thr Gln Leu Thr Val Leu
            100                 105                 110

<210> SEQ ID NO 17
<211> LENGTH: 449
<212> TYPE: PRT
<213> ORGANISM: Artificial Sequence
<220> FEATURE:
<223> OTHER INFORMATION: G1A8 heavy chain

<400> SEQUENCE: 17

Glu Val Gln Leu Leu Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Trp Gln Glu Leu Leu Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Ala Glu Pro Lys Ser Cys Asp Lys
    210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 18
<211> LENGTH: 216
<212> TYPE: PRT
<213> ORGANISM: Artificial Sequence
<220> FEATURE:
<223> OTHER INFORMATION: G1A8 light chain

<400> SEQUENCE: 18

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Trp Thr Arg Ser
                85                  90                  95

Ser Gly Leu Val Phe Gly Gly Gly Thr Gln Leu Thr Val Leu Gly Gln
            100                 105                 110

Pro Lys Ala Ala Pro Ser Val Thr Leu Phe Pro Pro Ser Ser Glu Glu
        115                 120                 125

```
Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
        180                 185                 190

Arg Ser Tyr Ser Cys Gln Val Thr His Glu Gly Ser Thr Val Glu Lys
    195                 200                 205

Thr Val Ala Pro Thr Glu Cys Ser
    210                 215

<210> SEQ ID NO 19
<211> LENGTH: 10
<212> TYPE: PRT
<213> ORGANISM: Artificial Sequence
<220> FEATURE:
<223> OTHER INFORMATION: HS29 HCDR3

<400> SEQUENCE: 19

Asp Val Tyr Gln Glu Leu Leu Phe Asp Tyr
1               5                   10

<210> SEQ ID NO 20
<211> LENGTH: 119
<212> TYPE: PRT
<213> ORGANISM: Artificial Sequence
<220> FEATURE:
<223> OTHER INFORMATION: HS29 VH

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Tyr Gln Glu Leu Leu Phe Asp Tyr Trp Gly Gln Gly
            100                 105                 110

Thr Leu Val Thr Val Ser Ser
        115

<210> SEQ ID NO 21
<211> LENGTH: 110
<212> TYPE: PRT
<213> ORGANISM: Artificial Sequence
<220> FEATURE:
<223> OTHER INFORMATION: HS29 VL

<400> SEQUENCE: 21

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
```

```
                20                  25                  30
Asn Tyr Val Ser Trp Tyr Gln Gln His Pro Gly Lys Ala Pro Lys Leu
                35                  40                  45

Met Ile Tyr Asp Val Ser Asn Arg Pro Ser Gly Val Pro Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Trp Thr Arg Ser
                 85                  90                  95

Ser Gly Leu Val Phe Gly Gly Gly Thr Gln Leu Thr Val Leu
                100                 105                 110

<210> SEQ ID NO 22
<211> LENGTH: 449
<212> TYPE: PRT
<213> ORGANISM: Artificial Sequence
<220> FEATURE:
<223> OTHER INFORMATION: HS29 heavy chain

<400> SEQUENCE: 22

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
                 35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Val Tyr Gln Glu Leu Leu Phe Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Ala Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
```

```
                275                 280                 285
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 23
<211> LENGTH: 216
<212> TYPE: PRT
<213> ORGANISM: Artificial Sequence
<220> FEATURE:
<223> OTHER INFORMATION: HS29 light chain

<400> SEQUENCE: 23

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Pro Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Trp Thr Arg Ser
                85                  90                  95

Ser Gly Leu Val Phe Gly Gly Gly Thr Gln Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190
```

```
Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 24
<211> LENGTH: 25
<212> TYPE: PRT
<213> ORGANISM: Artificial Sequence
<220> FEATURE:
<223> OTHER INFORMATION: N-terminal fragment of FGF19 with SGSGK tag

<400> SEQUENCE: 24

Arg Pro Leu Ala Phe Ser Asp Ala Gly Pro His Val His Tyr Gly Trp
1               5                   10                  15

Gly Asp Pro Ile Ser Gly Ser Gly Lys
            20                  25
```

ANTI-FGF19 ANTIBODIES

This application is a national stage filing under 35 U.S.C. § 371 of International Application No. PCT/CN2020/074154, filed on Feb. 2, 2020, which claims priority of International Application No. PCT/CN2019/074530, filed on Feb. 2, 2019. The contents of each of these applications are incorporated herein by reference.

FIELD OF THE INVENTION

Disclosed herein are antibodies and antigen-binding fragments thereof that bind to fibroblast growth factor 19 (FGF19), specifically to the majority of the residues comprising the antibodies' epitope at the N-terminus of FGF19. Also provided herein are compositions and uses of said antibodies, as well as methods of treating a disease or disorder caused by or related to abnormal FGF19-FGFR4 signaling, e.g. cancer, by administering the anti-FGF19 antibodies.

BACKGROUND OF THE INVENTION

Fibroblast growth factors (FGFs) are a family of proteins that have a diversity of functions in the development of organisms from nematode to human. In a number of normal developmental and physiological processes, FGF-FGFR (FGF receptor) signaling has been found to be critical, the dysregulation of which may have important roles in tumor development and progression (Turner N, Grose R. Nature Reviews Cancer, 2010, 10(2): 116, www.nature.com).

In human, fibroblast growth factor 19 (FGF19) is a bile acid-induced and ileum-derived peptide growth factor that functions to regulate bile acid metabolism by binding the hepatocyte-expressed FGF receptor 4 (FGFR4) and β-klotho (KLB) to repress the hepatic transcription of a gene encoding cholesterol-7-a-hydroxylase 1 (CYP7A1), an essential enzyme for bile acid biosynthesis (M. H. Xie et al., *Cytokine* 11, 729-735 (1999); J. A. Holt et al., *Genes & development* 17, 1581-1591 (2003); H. Kurosu et al., *The Journal of biological chemistry* 282, 26687-26695 (2007); and B. C. Lin et al., *The Journal of biological chemistry* 282, 27277-27284 (2007)). In addition to its bile-acid-regulatory function, clinical observations have demonstrated that both FGF19 and its cognate receptor FGFR4 are highly expressed in tumors as compared to adjacent non-tumorous tissue (E. T. Sawey et al., *Cancer Cell* 19, 347-358 (2011); K. Wang et al., *Hepatology* 58, 706-717 (2013); S. M. Ahn et al., *Hepatology* 60, 1972-1982 (2014); K. Schulze et al., *Nat Genet* 47, 505-511 (2015); M. H. Xie et al., (1999); L. R. Desnoyers et al., *Oncogene* 27, 85-97 (2008); and Y Li et al., *Oncotarget*, (2016)).

FGF19 was proposed to be a driver gene in the development of hepatocellular carcinoma (HCC), the most common type of liver cancer which accounts for approximately 90% of all liver cancer cases (J. M. Llovet et al., *Nat Rev Dis Primers* 2, 16018 (2016)). Liver cancer is the sixth most commonly diagnosed cancer globally, while ranks as the third most common cause of cancer-related deaths worldwide (F. Bray et al., *CA Cancer J Clin* 68, 394-424 (2018)). Several clinical studies have identified that HCC features highly focal amplification of fibroblast growth factor (FGF) 19 (E. T. Sawey et al., *Cancer Cell* 19, 347-358 (2011); K. Wang et al., *Hepatology* 58, 706-717 (2013); S. M. Ahn et al., *Hepatology* 60, 1972-1982 (2014); and K. Schulze et al., *Nat Genet* 47, 505-511 (2015)). The high expression of FGF19 and/or FGFR4 was found to promote tumor progression and could also be predictive of poor prognosis for HCC patients (S. Miura et al., *BMC Cancer* 12, 56 (2012); and J. Hyeon, S. Ahn, J. J. Lee, D. H. Song, C. K. Park, *Digestive diseases and sciences* 58, 1916-1922 (2013)). In transgenic mice, the over-expression of FGF19 caused hepatocellular dysplasia, neoplasia, and ultimately HCC (K. Nicholes et al., *Am J Pathol* 160, 2295-2307 (2002)), which was abolished in FGFR4 knockout mice (D. M. French et al., *PLoS One* 7, e36713 (2012)), thus mechanistically confirming the tumorigenic activity of aberrant FGF19/FGFR4 signaling, which provides a theoretical basis for the development of antagonistic agents targeting the FGF19/FGFR4 pathway as potential cancer treatment. However, several selective FGFR4 inhibitors under development for the treatment of HCC, have led to increased bile acid synthesis and liver toxicity either in preclinical animal models or early human clinical trials (M. Hagel et al., *Cancer Discov* 5, 424-437 (2015); R. Kim et al., *European Journal of Cancer* 69, S41 (2016); S. L. Chan et al., *Cancer research* 77, CT106-CT106 (2017); J. J. Joshi et al., *Cancer research* 77, 6999-7013 (2017); and B. Ruggeri et al., *Cancer research* 77, 1234-1234 (2017)). Efforts were made on developing drugs directly targeting FGF19 as a therapeutic target for treating HCC and a neutralizing anti-FGF19 antibody was obtained (WO2007136893A2, Genentech, Inc). Treatment of this anti-FGF19 antibody (1A6) prevented transgenic mice over-expressing FGF19 from developing HCC and such treatment also suppressed the growth of HCC xenografts in mice (E. T. Sawey et al., 2011, supra; and L. R. Desnoyers et al., 2008, supra). Unfortunately, however, in a toxicology study, administration of the humanized 1A6 antibody to cynomolgus monkeys increased hepatic transcription of CYP7A1 and elevated bile acid synthesis, thus dramatically altering bile acid metabolism and causing severe dose-related side effects such as reduced body weight, severe diarrhea, and low food consumption (R. Pai et al., *Toxicological sciences: an official journal of the Society of Toxicology* 126, 446-456 (2012)). Considering FGF19's role in the regulation of bile acid metabolism, antibodies targeting FGF19 may compromise its regular physiological function in this aspect and lead to unacceptable side effects. In view of these facts, a clinical therapy targeting FGF19 by an antibody will need to address such side effects.

The present invention meets the needs by providing anti-FGF19 antibodies specifically targeting to the N-terminus of FGF19, which shows potent efficacy as anti-HCC therapies while not adversely affecting FGF19's normal bile-acid-regulatory function.

All references, including scientific publications, patent application publications and patent publications, are incorporated herewith in their entity for all purposes.

SUMMARY OF THE INVENTION

The present invention is in part based on the discovery of a new binding region on FGF19, specifically at the N-terminus of FGF19, and the identification of anti-FGF19 antibodies which show potent anti-tumor activity on HCC and also have desirable safety for not impacting FGF19-mediated regulation of bile-acid synthesis by specifically binding to said binding region at N-terminus of FGF19. Accordingly, the present invention provides a new target on the N-terminus of FGF19 with therapeutic potential and also antibodies specifically binding to said target for the diagnosis, prevention, treatment and/or prognosis of pathological conditions related to and/or resulted from abnormal FGF19/FGFR4 signaling, specifically cancers related to and/or resulted from abnormal FGF19/FGFR4 signaling, including but not limited to HCC. Also provided are nucleic acid molecules, expression vectors and host cells comprising a nucleotide sequence encoding the antibody or the antigen-binding fragment thereof. The present invention also provides pharmaceutical compositions, methods, kits, articles of manufacture and medical uses related to modulation of FGF19/FGFR4 signaling pathway.

In the first aspect, the present disclosure provides an isolated antibody or an antigen-binding fragment thereof which binds to human fibroblast growth factor 19 (FGF19) and the binding depends on the N-terminus of FGF19. In one embodiment, the antibody or the antigen-binding fragment of the present application binds to an epitope located at amino acid residues at positions 38-45 of SEQ ID NO: 1. More specifically, the epitope comprises at least one, at least two, at least three, at least four, at least five, at least six, at least seven of the following residues of human FGF19 (SEQ ID NO: 1): W38, D40, P41, I42, R43, L44, R45. In a further embodiment, the antibody or the antigen-binding fragment of the present application binds to an epitope consists of amino acid residues at positions 38-45 of SEQ ID NO: 1 and at least one the following residues of human FGF19 (SEQ ID NO: 1): E81, P167, L169. In a further embodiment, the antibody or antigen-binding fragment thereof has at least one of the following properties: (i) binds to human FGF19 with a $K_D$ value of about $1\times10^{-9}$ M to about $1\times10^{-12}$ M as determined by surface plasmon resonance (e.g., BIACORE) or a similar technique; (ii) cross-reacts with cynomolgus monkey FGF19; (iii) blocks binding of human FGF19 to human FGFR4 and/or human FGFR4-KLB complex; (iv) suppresses FGF19-induced cell proliferation; (v) does not or minimally affect FGF19-suppressed CYP7A1 expression; and (vi) does not or marginally impair FGF19-maintained bile acid homeostasis.

In another embodiment of the first aspect, the anti-FGF19 antibody or the antigen-binding fragment of the present application comprises at least one, two or three heavy chain variable (VH) domain complementarity-determining regions (CDRs) comprising the amino acid sequence of SEQ ID Nos: 3, 4, 5, 13 or 19 or a variant thereof comprising one or more conservative substitutions. In another embodiment, the anti-FGF19 antibody or the antigen-binding fragment of the present application comprises at least one, two or three light chain variable (VL) domain CDRs comprising the amino acid sequence of SEQ ID Nos: 6, 7, 8 or 14 or variants thereof comprising one or more conservative substitutions. In another embodiment, the anti-FGF19 antibody or the antigen-binding fragment of the present application comprises at least one, two or three heavy chain variable (VH) domain CDRs comprising the amino acid sequence of SEQ ID Nos: 3, 4, 5, 13 or 19 or a variant thereof comprising one or more conservative substitutions, and at least one, two or three light chain variable (VL) domain CDRs comprising the amino acid sequence of SEQ ID Nos: 6, 7, 8 or 14 or variants thereof comprising one or more conservative substitutions. In a further embodiment, the antibody or antigen-binding fragment thereof has at least one of the following properties: (i) binds to human FGF19 with a $K_D$ value of about $1\times10^{-9}$ M to about $1\times10^{-12}$ M as determined by surface plasmon resonance (e.g., BIACORE) or a similar technique; (ii) cross-reacts with cynomolgus monkey FGF19; (iii) blocks binding of human FGF19 to human FGFR4 and/or human FGFR4-KLB complex; (iv) suppresses FGF19-induced cell proliferation; (v) does not or minimally affect FGF19-suppressed CYP7A1 expression; and (vi) does not or marginally impair FGF19-maintained bile acid homeostasis.

In one embodiment, the anti-FGF19 antibody or the antigen-binding fragment of the present application comprises (a) a heavy chain variable (VH) domain comprising an HCDR1 (heavy chain complementarity-determining region 1) having the amino acid sequence of SEQ ID NO: 3 or a variant thereof comprising one or more conservative substitutions, an HCDR2 having the amino acid sequence of SEQ ID NO: 4 or a variant thereof comprising one or more conservative substitutions, and an HCDR3 having an amino acid sequence of SEQ ID NOs: 5, SEQ ID NO: 13, SEQ ID NO: 19 or a variant thereof comprising one or more conservative substitutions; and/or (b) a light chain variable (VL) domain comprising an LCDR1 (light chain complementarity-determining region 1) having the amino acid sequence of SEQ ID NO: 6 or a variant thereof comprising one or more conservative substitutions, an LCDR2 having the amino acid sequence of SEQ ID NO: 7 or a variant thereof comprising one or more conservative substitutions, and an LCDR3 having an amino acid sequence of SEQ ID NO: 8, SEQ ID NO: 14 or a variant thereof comprising one or more conservative substitutions.

In one embodiment, the anti-FGF19 antibody or the antigen-binding fragment of the present application comprises (a) a heavy chain variable (VH) domain comprising an HCDR1 having the amino acid sequence of SEQ ID NO: 3, an HCDR2 having the amino acid sequence of SEQ ID NO: 4, and an HCDR3 having an amino acid sequence of SEQ ID NOs: 5, SEQ ID NO: 13 or SEQ ID NO: 19; and/or (b) a light chain variable (VL) domain comprising an LCDR1 having the amino acid sequence of SEQ ID NO: 6, an LCDR2 having the amino acid sequence of SEQ ID NO: 7, and an LCDR3 having an amino acid sequence of SEQ ID NO: 8 or SEQ ID NO: 14.

In one embodiment, the anti-FGF19 antibody or the antigen-binding fragment of the present application comprises (a) a heavy chain variable (VH) domain comprising an HCDR1 having the amino acid sequence of SEQ ID NO: 3 or a variant thereof comprising one or more conservative substitutions, an HCDR2 having the amino acid sequence of SEQ ID NO: 4 or a variant thereof comprising one or more conservative substitutions, and an HCDR3 having an amino acid sequence of SEQ ID NOs: 5 or a variant thereof comprising one or more conservative substitutions; and/or (b) a light chain variable (VL) domain comprising an LCDR1 having the amino acid sequence of SEQ ID NO: 6 or a variant thereof comprising one or more conservative substitutions, an LCDR2 having the amino acid sequence of SEQ ID NO: 7 or a variant thereof comprising one or more conservative substitutions, and an LCDR3 having an amino acid sequence of SEQ ID NO: 8 or a variant thereof comprising one or more conservative substitutions. In a more specific embodiment, the anti-FGF19 antibody or the antigen-binding fragment of the present application comprises (a) a heavy chain variable (VH) domain comprising an HCDR1 having the amino acid sequence of SEQ ID NO: 3, an HCDR2 having the amino acid sequence of SEQ ID NO: 4, and an HCDR3 having an amino acid sequence of SEQ ID NOs: 5; and/or (b) a light chain variable (VL) domain comprising an LCDR1 having the amino acid sequence of SEQ ID NO: 6, an LCDR2 having the amino acid sequence of SEQ ID NO: 7, and an LCDR3 having an amino acid sequence of SEQ ID NO: 8.

In one embodiment, the anti-FGF19 antibody or the antigen-binding fragment of the present application comprises (a) a heavy chain variable (VH) domain comprising an HCDR1 having the amino acid sequence of SEQ ID NO: 3 or a variant thereof comprising one or more conservative substitutions, an HCDR2 having the amino acid sequence of SEQ ID NO: 4 or a variant thereof comprising one or more conservative substitutions, and an HCDR3 having an amino acid sequence of SEQ ID NOs: 13 or a variant thereof comprising one or more conservative substitutions; and/or (b) a light chain variable (VL) domain comprising an LCDR1 having the amino acid sequence of SEQ ID NO: 6 or a variant thereof comprising one or more conservative substitutions, an LCDR2 having the amino acid sequence of SEQ ID NO: 7 or a variant thereof comprising one or more conservative substitutions, and an LCDR3 having an amino acid sequence of SEQ ID NO: 14 or a variant thereof comprising one or more conservative substitutions. In a more specific embodiment, the anti-FGF19 antibody or the antigen-binding fragment of the present application comprises (a) a heavy chain variable (VH) domain comprising an HCDR1 having the amino acid sequence of SEQ ID NO: 3, an HCDR2 having the amino acid sequence of SEQ ID NO: 4, and an HCDR3 having an amino acid sequence of SEQ ID NOs: 13; and/or (b) a light chain variable (VL) domain comprising an LCDR1 having the amino acid sequence of SEQ ID NO: 6, an LCDR2 having the amino acid sequence of SEQ ID NO: 7, and an LCDR3 having an amino acid sequence of SEQ ID NO: 14.

In one embodiment, the anti-FGF19 antibody or the antigen-binding fragment of the present application comprises (a) a heavy chain variable (VH) domain comprising an HCDR1 having the amino acid sequence of SEQ ID NO: 3 or a variant thereof comprising one or more conservative substitutions, an HCDR2 having the amino acid sequence of SEQ ID NO: 4 or a variant thereof comprising one or more conservative substitutions, and an HCDR3 having an amino acid sequence of SEQ ID NOs: 19 or a variant thereof comprising one or more conservative substitutions; and/or (b) a light chain variable (VL) domain comprising an LCDR1 having the amino acid sequence of SEQ ID NO: 6 or a variant thereof comprising one or more conservative substitutions, an LCDR2 having the amino acid sequence of SEQ ID NO: 7 or a variant thereof comprising one or more conservative substitutions, and an LCDR3 having an amino acid sequence of SEQ ID NO: 14 or a variant thereof comprising one or more conservative substitutions. In a more specific embodiment, the anti-FGF19 antibody or the antigen-binding fragment of the present application comprises (a) a heavy chain variable (VH) domain comprising an HCDR1 having the amino acid sequence of SEQ ID NO: 3, an HCDR2 having the amino acid sequence of SEQ ID NO: 4, and an HCDR3 having an amino acid sequence of SEQ ID NOs: 19; and/or (b) a light chain variable (VL) domain comprising an LCDR1 having the amino acid sequence of SEQ ID NO: 6, an LCDR2 having the amino acid sequence of SEQ ID NO: 7, and an LCDR3 having an amino acid sequence of SEQ ID NO: 14.

In one preferred embodiment, the anti-FGF19 antibody or the antigen-binding fragment of the present application comprises a heavy chain variable domain having at least 95%, 96%, 97%, 98%, 99% or 100% sequence identity to the amino acid sequence of SEQ ID NO: 9, 15, or 20; and/or a light chain variable domain having at least 95%, 96%, 97%, 98%, 99% or 100% sequence identity to the amino acid sequence of SEQ ID NO: 10, 16, or 21. In one preferred embodiment, the anti-FGF19 antibody or the antigen-binding fragment of the present application comprises a heavy chain variable domain having the amino acid sequence of SEQ ID NO: 9, 15, or 20 and a light chain variable domain having the amino acid sequence of SEQ ID NO: 10, 16, or 21.

In one preferred embodiment, the anti-FGF19 antibody or the antigen-binding fragment of the present application comprises (a) a heavy chain variable domain having at least 95%, 96%, 97%, 98%, 99% or 100% sequence identity to the amino acid sequence of SEQ ID NO: 9, and/or a light chain variable domain having at least 95%, 96%, 97%, 98%, 99% or 100% sequence identity to the amino acid sequence of SEQ ID NO:10; (b) a heavy chain variable domain having at least 95%, 96%, 97%, 98%, 99% or 100% sequence identity to the amino acid sequence of SEQ ID NO: 15, and/or a light chain variable domain having at least 95%, 96%, 97%, 98%, 99% or 100% sequence identity to the amino acid sequence of SEQ ID NO: 16; or (c) a heavy chain variable domain having at least 95%, 96%, 97%, 98%, 99% or 100% sequence identity to the amino acid sequence of SEQ ID NO: 20, and a light chain variable domain having at least 95%, 96%, 97%, 98%, 99% or 100% sequence identity to the amino acid sequence of SEQ ID NO:21. In one preferred embodiment, the anti-FGF19 antibody or the antigen-binding fragment of the present application comprises (a) a heavy chain variable domain comprising the amino acid sequence of SEQ ID NO: 9, and/or a light chain variable domain comprising the amino acid sequence of SEQ ID NO: 10; (b) a heavy chain variable domain comprising the amino acid sequence of SEQ ID NO:15, and/or a light chain variable domain comprising the amino acid sequence of SEQ ID NO:16; or (c) a heavy chain variable domain comprising the amino acid sequence of SEQ ID NO:20, and/or a light chain variable domain comprising the amino acid sequence of SEQ ID NO: 21.

In one preferred embodiment, the anti-FGF19 antibody or the antigen-binding fragment of the present application comprises a heavy chain having at least 95%, 96%, 97%, 98%, 99% or 100% sequence identity to the amino acid sequence of SEQ ID NO: 11, 17 or 22; and/or a light chain having at least 95%, 96%, 97%, 98%, 99% or 100% sequence identity to the amino acid sequence of SEQ ID NO: 12, 18 or 23. In one preferred embodiment, the anti-FGF19 antibody or the antigen-binding fragment of the present application comprises a heavy chain having the amino acid sequence of SEQ ID NO:11, 17 or 22; and/or a light chain having the amino acid sequence of SEQ ID NO: 12, 18 or 23.

In one preferred embodiment, the anti-FGF19 antibody or the antigen-binding fragment of the present application comprises (a) a heavy chain having at least 95%, 96%, 97%, 98%, 99% or 100% sequence identity to the amino acid sequence of SEQ ID NO: 11, and/or a light chain having at least 95%, 96%, 97%, 98%, 99% or 100% sequence identity to the amino acid sequence of SEQ ID NO: 12; (b) a heavy chain having at least 95%, 96%, 97%, 98%, 99% or 100% sequence identity to the amino acid sequence of SEQ ID NO: 17, and/or a light chain having at least 95%, 96%, 97%, 98%, 99% or 100% sequence identity to the amino acid sequence of SEQ ID NO: 18, or (c) a heavy chain having at least 95%, 96%, 97%, 98%, 99% or 100% sequence identity to the amino acid sequence of SEQ ID NO: 22, and/or a light chain having at least 95%, 96%, 97%, 98%, 99% or 100% sequence identity to the amino acid sequence of SEQ ID NO: 23. In one preferred embodiment, the anti-FGF19 antibody or the antigen-binding fragment of the present application comprises (a) a heavy chain having the amino acid sequence of SEQ ID NO: 11, and/or a light chain having the amino acid sequence of SEQ ID NO: 12; (b) a heavy chain having the amino acid sequence of SEQ ID NO: 17, and/or a light chain having the amino acid sequence of SEQ ID NO: 18, or (c) a heavy chain having the amino acid sequence of SEQ ID NO: 22, and/or a light chain having the amino acid sequence of SEQ ID NO: 23.

In one embodiment, the present application provides an anti-FGF19 antibody or the antigen-binding fragment that competes for binding to human FGF19 with an antibody comprising a heavy chain variable (VH) domain comprising an HCDR1 having the amino acid sequence of SEQ ID NO: 3, an HCDR2 having the amino acid sequence of SEQ ID NO: 4, and an HCDR3 having an amino acid sequence of SEQ ID NOs: 5; and a light chain variable (VL) domain comprising an LCDR1 having the amino acid sequence of SEQ ID NO: 6, an LCDR2 having the amino acid sequence of SEQ ID NO: 7, and an LCDR3 having an amino acid sequence of SEQ ID NO: 8. In a more specific embodiment, the present application provides an anti-FGF19 antibody or the antigen-binding fragment that competes for binding to human FGF19 with an antibody comprising a heavy chain variable domain having the amino acid sequence of SEQ ID NO: 9 and a light chain variable domain comprising the amino acid sequence of SEQ ID NO: 10. More preferably, said antibody or antigen-binding fragment thereof has at least one of the following properties: (i) binds to human FGF19 with a $K_D$ value of about $1 \times 10^{-9}$ M to about $1 \times 10^{-12}$ M as determined by surface plasmon resonance (e.g., BIACORE) or a similar technique; (ii) cross-reacts with cynomolgus monkey FGF19; (iii) blocks binding of human FGF19 to human FGFR4 and/or human FGFR4-KLB complex; (iv) suppresses FGF19-induced cell proliferation; (v) does not or minimally affect FGF19-suppressed CYP7A1 expression; and (vi) does not or marginally impair FGF19-maintained bile acid homeostasis.

In one embodiment, the present application provides an anti-FGF19 antibody or the antigen-binding fragment that competes for binding to human FGF19 with an antibody comprising a heavy chain variable (VH) domain comprising an HCDR1 having the amino acid sequence of SEQ ID NO: 3, an HCDR2 having the amino acid sequence of SEQ ID NO: 4, and an HCDR3 having an amino acid sequence of SEQ ID NO: 13; and a light chain variable (VL) domain comprising an LCDR1 having the amino acid sequence of SEQ ID NO: 6, an LCDR2 having the amino acid sequence of SEQ ID NO: 7, and an LCDR3 having an amino acid sequence of SEQ ID NO: 14. In a more specific embodiment, the present application provides an anti-FGF19 antibody or the antigen-binding fragment that competes for binding to human FGF19 with an antibody comprising a heavy chain variable domain having the amino acid sequence of SEQ ID NO:15 and a light chain variable domain comprising the amino acid sequence of SEQ ID NO: 16. More preferably, said antibody or antigen-binding fragment thereof has at least one of the following properties: (i) binds to human FGF19 with a $K_D$ value of about $1 \times 10^{-9}$ M to about $1 \times 10^{-12}$ M as determined by surface plasmon resonance (e.g., BIACORE) or a similar technique; (ii) cross-reacts with cynomolgus monkey FGF19; (iii) blocks binding of human FGF19 to human FGFR4 and/or human FGFR4-KLB complex; (iv) suppresses FGF19-induced cell proliferation; (v) does not or minimally affect FGF19-suppressed CYP7A1 expression; and (vi) does not or marginally impair FGF19-maintained bile acid homeostasis.

In one embodiment, the present application provides an anti-FGF19 antibody or the antigen-binding fragment that competes for binding to human FGF19 with an antibody comprising a heavy chain variable (VH) domain comprising an HCDR1 having the amino acid sequence of SEQ ID NO: 3, an HCDR2 having the amino acid sequence of SEQ ID NO: 4, and an HCDR3 having an amino acid sequence of SEQ ID NO: 19; and a light chain variable (VL) domain comprising an LCDR1 having the amino acid sequence of SEQ ID NO: 6, an LCDR2 having the amino acid sequence of SEQ ID NO: 7, and an LCDR3 having an amino acid sequence of SEQ ID NO: 14. In a more specific embodiment, the present application provides an anti-FGF19 antibody or the antigen-binding fragment that competes for binding to human FGF19 with an antibody comprising a heavy chain variable domain having the amino acid sequence of SEQ ID NO: 20 and a light chain variable domain comprising the amino acid sequence of SEQ ID NO: 21. More preferably, said antibody or antigen-binding fragment thereof has at least one of the following properties: (i) binds to human FGF19 with a $K_D$ value of about $1 \times 10^{-9}$ M to about $1 \times 10^{-12}$ M as determined by surface plasmon resonance (e.g., BIACORE) or a similar technique; (ii) cross-reacts with cynomolgus monkey FGF19; (iii) blocks binding of human FGF19 to human FGFR4 and/or human FGFR4-KLB complex; (iv) suppresses FGF19-induced cell proliferation; (v) does not or minimally affect FGF19-suppressed CYP7A1 expression; and (vi) does not or marginally impair FGF19-maintained bile acid homeostasis.

In one embodiment, the present application provides an anti-FGF19 antibody or the antigen-binding fragment that binds to the same epitope of human FGF19 as an antibody comprising a heavy chain variable (VH) domain comprising an HCDR1 having the amino acid sequence of SEQ ID NO: 3, an HCDR2 having the amino acid sequence of SEQ ID NO: 4, and an HCDR3 having an amino acid sequence of SEQ ID NO: 5; and a light chain variable (VL) domain comprising an LCDR1 having the amino acid sequence of SEQ ID NO: 6, an LCDR2 having the amino acid sequence of SEQ ID NO: 7, and an LCDR3 having an amino acid sequence of SEQ ID NO: 8. In a more specific embodiment, the present application provides an anti-FGF19 antibody or the antigen-binding fragment that binds to the same epitope of human FGF19 as an antibody comprising a heavy chain variable domain comprising the amino acid sequence of SEQ ID NO: 9 and a light chain variable domain comprising the amino acid sequence of SEQ ID NO: 10. More preferably, said antibody or antigen-binding fragment thereof has at least one of the following properties: (i) binds to human FGF19 with a $K_D$ value of about $1 \times 10^{-9}$ M to about $1 \times 10^{-12}$ M as determined by surface plasmon resonance (e.g., BIACORE) or a similar technique; (ii) cross-reacts with cynomolgus monkey FGF19; (iii) blocks binding of human FGF19 to human FGFR4 and/or human FGFR4-KLB complex; (iv) suppresses FGF19-induced cell proliferation; (v) does not or minimally affect FGF19-suppressed CYP7A1 expression; and (vi) does not or marginally impair FGF19-maintained bile acid homeostasis.

In one embodiment, the present application provides an anti-FGF19 antibody or the antigen-binding fragment that binds to the same epitope of human FGF19 as an antibody comprising a heavy chain variable (VH) domain comprising an HCDR1 having the amino acid sequence of SEQ ID NO: 3, an HCDR2 having the amino acid sequence of SEQ ID NO: 4, and an HCDR3 having an amino acid sequence of SEQ ID NO: 13; and a light chain variable (VL) domain comprising an LCDR1 having the amino acid sequence of SEQ ID NO: 6, an LCDR2 having the amino acid sequence of SEQ ID NO: 7, and an LCDR3 having an amino acid sequence of SEQ ID NO: 14. In a more specific embodiment, the present application provides an anti-FGF19 antibody or the antigen-binding fragment that binds to the same epitope of human FGF19 as an antibody comprising a heavy chain variable domain comprising the amino acid sequence of SEQ ID NO:15 and a light chain variable domain comprising the amino acid sequence of SEQ ID NO: 16. More preferably, said antibody or antigen-binding fragment thereof has at least one of the following properties: (i) binds to human FGF19 with a $K_D$ value of about $1\times10^{-9}$M to about $1\times10^{-12}$M as determined by surface plasmon resonance (e.g., BIACORE) or a similar technique; (ii) cross-reacts with cynomolgus monkey FGF19; (iii) blocks binding of human FGF19 to human FGFR4 and/or human FGFR4-KLB complex; (iv) suppresses FGF19-induced cell proliferation; (v) does not or minimally affect FGF19-suppressed CYP7A1 expression; and (vi) does not or marginally impair FGF19-maintained bile acid homeostasis.

In one embodiment, the present application provides an anti-FGF19 antibody or the antigen-binding fragment that binds to the same epitope of human FGF19 as an antibody comprising a heavy chain variable (VH) domain comprising an HCDR1 having the amino acid sequence of SEQ ID NO: 3, an HCDR2 having the amino acid sequence of SEQ ID NO: 4, and an HCDR3 having an amino acid sequence of SEQ ID NOs: 19; and a light chain variable (VL) domain comprising an LCDR1 having the amino acid sequence of SEQ ID NO: 6, an LCDR2 having the amino acid sequence of SEQ ID NO: 7, and an LCDR3 having an amino acid sequence of SEQ ID NO: 14. In a more specific embodiment, the present application provides an anti-FGF19 antibody or the antigen-binding fragment that binds to the same epitope of human FGF19 as an antibody comprising a heavy chain variable domain comprising the amino acid sequence of SEQ ID NO:20 and a light chain variable domain comprising the amino acid sequence of SEQ ID NO: 21. More preferably, said antibody or antigen-binding fragment thereof has at least one of the following properties: (i) binds to human FGF19 with a $K_D$ value of about $1\times10^{-9}$ M to about $1\times10^{-12}$ M as determined by surface plasmon resonance (e.g., BIACORE) or a similar technique; (ii) cross-reacts with cynomolgus monkey FGF19; (iii) blocks binding of human FGF19 to human FGFR4 and/or human FGFR4-KLB complex; (iv) suppresses FGF19-induced cell proliferation; (v) does not or minimally affect FGF19-suppressed CYP7A1 expression; and (vi) does not or marginally impair FGF19-maintained bile acid homeostasis.

In one embodiment, the anti-FGF19 antibody is a human antibody. In one embodiments, the anti-FGF19 antibody is a human monoclonal antibody (mAb).

In one embodiment, the anti-FGF19 antibody is a Fab, F(ab')2, Fv, or a single chain Fv (ScFv).

In one embodiment, the anti-FGF19 antibody comprises a heavy chain constant region of the subclass of IgG1, IgG2, IgG3, IgG4 or a variant thereof, and a light chain constant region of the type of kappa or lambda or a variant thereof.

In one embodiment, the anti-FGF19 antibody is an isolated antibody. In one embodiment, the anti-FGF19 antibody is a recombinant antibody.

In a preferred embodiment, the present antibody or antigen-binding fragment of the first aspect of the present application is for treating a disease or a disorder caused by or related to abnormal FGF19-FGFR4 signaling, comprising administering to a subject in need thereof. In a specific embodiment, the disease or disorder is cancer caused by or related to abnormal FGF19-FGFR4 signaling. In a more specific embodiment, the cancer is hepatocellular carcinoma (HCC).

In the second aspect, the present disclosure provides a composition, e.g., a pharmaceutical composition, comprising the anti-FGF19 antibody or antigen-binding fragment of the first aspect of the present application, and a pharmaceutically acceptable excipient. In a preferred embodiment, the pharmaceutical composition comprises a therapeutically efficient amount of the anti-FGF19 antibody or antigen-binding fragment.

In the third aspect, the present disclosure provides a kit comprising the anti-FGF19 antibody or antigen-binding fragment of the first aspect of the present application, or the composition of the second aspect of the present application. In a preferred embodiment, the kit comprises a therapeutically efficient amount of the anti-FGF19 antibody or antigen-binding fragment.

In the fourth aspect, the present disclosure provides a method for preventing or treating a disease or a disorder caused by or related to abnormal FGF19-FGFR4 signaling, comprising administering to a subject in need thereof an therapeutically effective amount of the antibody or antigen-binding fragment of the first aspect of the present application, or the pharmaceutical composition of the second aspect of the present application. In a specific embodiment, the disease or disorder is cancer caused by or related to abnormal FGF19-FGFR4 signaling. In a more specific embodiment, the cancer is hepatocellular carcinoma (HCC).

In a fifth aspect, the present disclosure provides a method for preventing recurrence of a disease or a disorder caused by or related to abnormal FGF19-FGFR4 signaling, comprising administering to a subject in need thereof an therapeutically effective amount of the antibody or antigen-binding fragment of the first aspect of the present application, or the pharmaceutical composition of the second aspect of the present application. In a specific embodiment, the disease or disorder is cancer caused by or related to abnormal FGF19-FGFR4 signaling. In a more specific embodiment, the cancer is hepatocellular carcinoma (HCC). In one embodiment, the recurrence of the disease or disorder occurs after surgery.

In the sixth aspect, the present disclosure provides use of the antibody or antigen-binding fragment of the first aspect of the present application, or the pharmaceutical composition of the second aspect of the present application for treating various disorders or diseases described herein, or for preventing recurrence of various disorders or diseases described herein. In a specific embodiment, the disease or disorder is a disease or a disorder caused by or related to abnormal FGF19-FGFR4 signaling, preferably cancer caused by or related to abnormal FGF19-FGFR4 signaling. In a more specific embodiment, the cancer is hepatocellular carcinoma (HCC). In one embodiment, the recurrence of the disease or disorder occurs after surgery.

In the seventh aspect, the present disclosure provides use of the antibody or antigen-binding fragment of the first aspect of the present application, or the pharmaceutical composition of the second aspect of the present application in the manufacture of a medicament for treating various disorders or diseases described herein, or for preventing recurrence of various disorders or diseases described herein. In a specific embodiment, the disease or disorder is a disease or a disorder caused by or related to abnormal FGF19-FGFR4 signaling, preferably cancer caused by or related to abnormal FGF19-FGFR4 signaling. In a more specific embodiment, the cancer is hepatocellular carcinoma (HCC). In one embodiment, the recurrence of the disease or disorder occurs after surgery. In one embodiment, the recurrence of the disease or disorder occurs after surgery.

DETAIL DESCRIPTION OF THE INVENTION

Definitions

Figure 1:
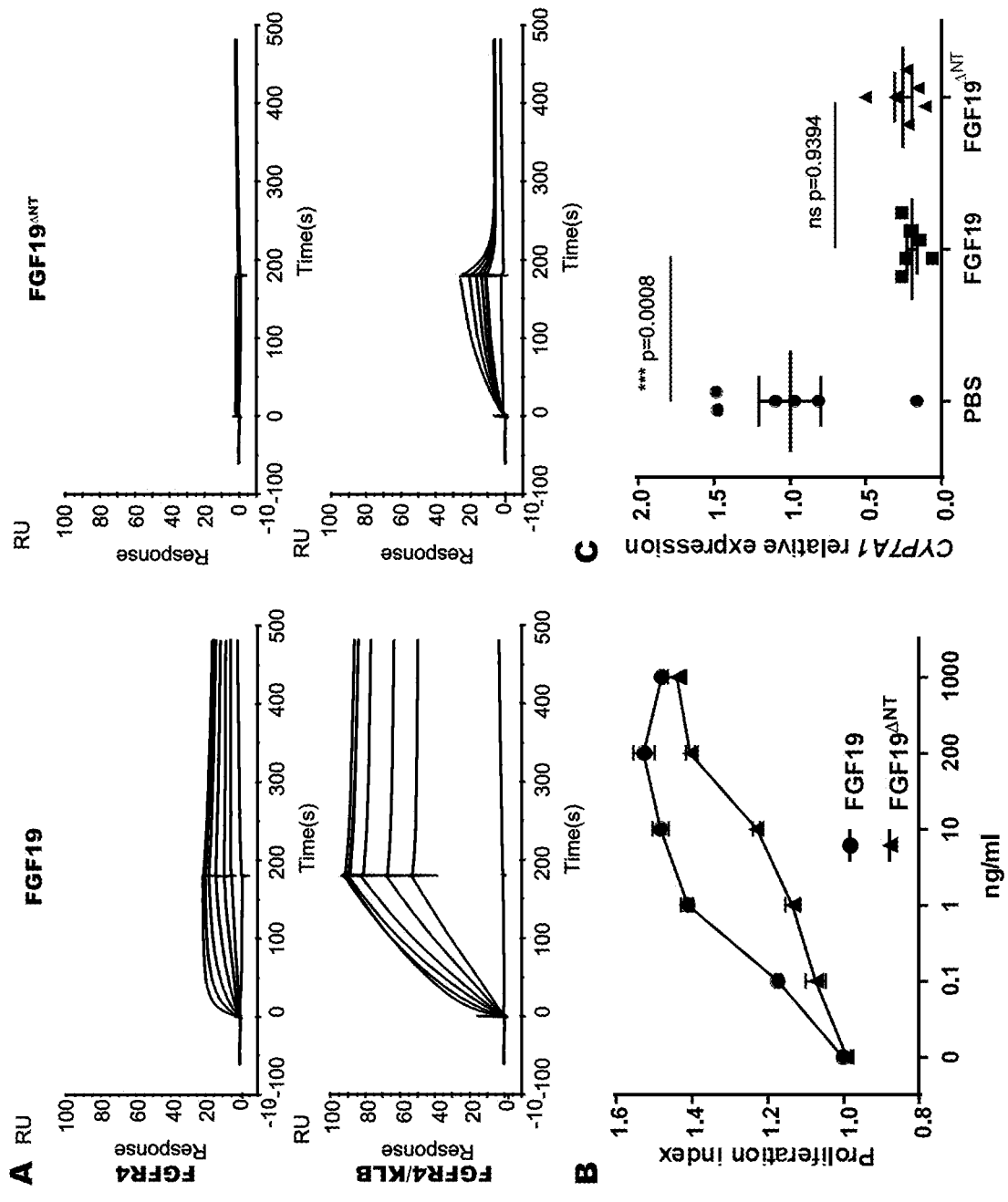
FIG. 1A-C Dispensable role of the N-terminus of FGF19 in mediating FGF19's activity. (A) Binding affinity of FGF19 or FGF19$^{\Delta NT}$ (the N-terminus deletion variant of FGF19) to FGFR4 or FGFR4-KLB complex is shown. The N-terminus deletion variant FGF19$^{\Delta NT}$ showed a reduced binding affinity to FGFR4. FGFR4-hFc was captured as a ligand on the sensor chip in Biacore. Interactions between the ligand FGFR4 and analyte FGF19 or FGF19$^{\Delta NT}$ were measured in the presence of 20 μg/ml Heparin. Analytes FGF19 and FGF19$^{\Delta NT}$ were in 2-fold serial dilutions from 1000 nM. (B) N-terminus deletion variant FGF19$^{\Delta NT}$ showed a reduced activity in inducing cell proliferation. Hep3B was cultured with different concentrations of FGF19 or FGF19$^{\Delta NT}$ in 1% FBS containing DMEM. (C) N-terminus deletion variant FGF19$^{\Delta NT}$ remained the ability to suppress CYP7A1 gene expression in vivo. C57BL/6 mice were fasted before intraperitoneal injection with indicated treatments. Hepatic gene expression of CYP7A1 was analyzed by qPCR. Each treatment group consisted of 3 male and 3 female mice.

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

In the context of the present disclosure, unless being otherwise indicated, the wording "comprise", and variations thereof such as "comprises" and "comprising" will be understood to imply the inclusion of a stated element, e.g. an amino acid sequence, a nucleotide sequence, a property, a step or a group thereof, but not the exclusion of any other elements, e.g. amino acid sequences, nucleotide sequences, properties and steps. When used herein the term "comprise" or any variation thereof can be substituted with the term "contain", "include" or sometimes "have" or equivalent variation thereof. In certain embodiments, the wording "comprise" also includes the scenario of "consisting of".

The term "FGF19" as used herein refers to the ileum-derived hormone fibroblast growth factor 19, which is a high affinity ligand for FGFR4 (fibroblast growth factor receptor 4). As stated above, FGF19 plays an important role in the regulation of bile acid synthesis among others by inhibiting transcription of CYP7A1 in liver through the FGFR4/Klotho-β receptor complexes. In the context of the present application, unless specifically indicated, FGF19 means human FGF19. The ortholog of human FGF19 in mouse is FGF15. The amino acid sequence of FGF19, e.g., human FGF19, and the nucleotide sequence encoding the same, are known in the art. FGFs have a homologous core region formed by 12 antiparallel β-strands flanked by divergent N-terminus and C-terminus (A. Beenken and M. Mohammadi, *Nature reviews. Drug discovery* 8, 235-253 (2009)). Primary sequence variations among the N- and C-termini of various FGFs account for their different biology activities (N. Itoh and D. M. Ornitz, *J Biochem* 149, 121-130 (2011); R. Goetz and M. Mohammadi, *Nat Rev Mol Cell Biol* 14, 166-180 (2013)).

Antibody and Antigen-Binding Fragment Thereof

Unless being otherwise indicated, the term "antibody" as used herein encompasses antibodies as well as antibody fragments in the broadest sense, as long as it recognizes and binds to human FGF19. In particular, the antibody of the present application binds to the N-terminus of human FGF19, specifically amino acid residues 38-45 of FGF19 having the amino acid sequence of SEQ ID NO: 1. The antibody of the present application in general refers to a monospecific antibody. But the present application also contemplates an antibody with heterologous specificity (heterospecific) or a multispecific antibody. Antibody binds to specific antigenic determinants or epitopes by means of specific binding sites. An "antibody fragment" means a portion of a full length antibody, usually comprising the binding or variable region for the antigen. Examples of antibody fragments can include Fab, Fab', F(ab')2 and Fv fragments; diabodies; linear antibodies; single-chain antibody molecules; and multispecific antibodies formed from antibody fragments.

The most commonly seen basic structure of an antibody is a tetramer. Each tetramer includes two identical pairs of polypeptide chains, each pair having one smaller chain designated as the "light chain" (about 25 kDa) and one bigger chain designated as the "heavy chain" (about 50-70 kDa). At the amino-terminus of each chain, it includes a variable domain of about 100 to 110 or more amino acids primarily responsible for antigen recognition. The carboxy-terminal portion of the heavy chain may define a constant region primarily responsible for effector function. Typically, light chains of human antibodies are classified as kappa and lambda light chains. Furthermore, heavy chains of human antibodies are typically classified as α, δ, ε, γ, or μ, and define the antibody's isotypes as IgA, IgD, IgE, IgG, and IgM, respectively, and subclass thereof, for example, IgG1, IgG2, IgG3, and IgG4. The variable regions/domains of each light/heavy chain (VL/VH) pair form the antibody binding site. Accordingly, an intact antibody usually has two binding sites.

The term "hypervariable domain" means the amino acid residues of an antibody that are responsible for antigen-binding. The hypervariable domain comprises amino acid residues from a "complementarity determining region (CDR)" (i.e., LCDR1, LCDR2 and LCDR3 in the light chain variable domain and HCDR1, HCDR2 and HCDR3 in the heavy chain variable domain). Typically, the variable domains of both the heavy and light chains comprise three hypervariable domains, namely CDRs, which are located between relatively conserved "framework regions" or "FR". The CDRs are usually aligned by the framework regions, enabling binding to a specific epitope. In general, from N-terminal to C-terminal, both light and heavy chain variable domains comprise FR-1 (or FR1), CDR-1 (or CDR1), FR-2 (FR2), CDR-2 (CDR2), FR-3 (or FR3), CDR-3 (CDR3), and FR-4 (or FR4). Kabat numbering system is used for the amino acid residues of the antibody unless indicated otherwise (Kabat et al., Sequence of proteins of immunological interest, $5^{th}$ ed., Public Health Service, National Institute of Health, Bethesda, MD (1991)).

Unless otherwise indicated, "antibody fragment", "target-binding fragment" and "antigen-binding fragment" are interchangeable in the context of the present application and mean antibody fragments that retain the ability to bind specifically to the antigen (FGF19, or particularly N-terminus of FGF19) bound by the full-length antibody, e.g. fragments that retain one or more CDR regions. Examples of antigen binding fragments include, but not limited to, Fab, Fab', F(ab')2, and Fv fragments; diabodies; linear antibodies; single-chain antibody molecules, e.g., single chain Fv (ScFv); nanobodies and multispecific antibodies formed from antibody fragments.

By "specific binding" or "specifically bind to", it means that an antibody exhibits preferential binding to a certain target as compared to other proteins, but this specificity does not require absolute binding specificity. An antibody is considered "specific" for its intended target if its binding is determinative of the presence of the target protein in a sample, e.g. without producing undesired results such as false positives. The antibody or an antigen binding fragment thereof of the present invention will bind to the target protein with an affinity that is at least 2-fold greater, preferably at least 10-fold greater, more preferably at least 20-fold greater, and most preferably at least 100-fold greater than the affinity with non-target proteins. Alternatively or additionally, the antibody or an antigen binding fragment thereof of the present invention will have a binding affinity to its target protein as represented by a KD value of lower than $1 \times 10^{-8}$ M, lower than $1\times10^{-9}$ M (1 nM), lower than $1\times10^{-10}$ M, lower than $1\times10^{-11}$ M, or even lower than $1\times10^{-12}$ M (1 pM). An antibody of the present application is said to bind specifically to a polypeptide comprising a given amino acid sequence, e.g. the amino acid sequence of a mature human FGF19 or N-terminal residues 38-45 of human FGF19, if it binds to polypeptides comprising that sequence but does not bind to proteins lacking that sequence.

The term "human antibody" as used herein means an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" means an antibody comprising only mouse or rat immunoglobulin protein sequences, respectively.

The term "monoclonal antibody" or "mAb" or "Mab" as used herein refers to a population of substantially homogeneous antibodies, which means that the antibody molecules comprised in the population are identical in amino acid sequence except for possible naturally occurring mutations that may be present in minor amounts. By "monoclonal", it indicates the character of the antibody as being obtained from a substantially homogeneous population of antibodies, and is not to be construed as requiring the antibody to be produced by any particular method. Monoclonal antibodies (mAbs) may be obtained by conventional methods known in the art. See, for example Kohler G et al., Nature 1975 256:495-497; U.S. Pat. No. 4,376,110; Ausubel F M et al., CURRENT PROTOCOLS IN MOLECULAR BIOLOGY 1992; Harlow E et al., ANTIBODIES: A LABORATORY MANUAL, Cold spring Harbor Laboratory 1988; and Colligan J E et al., CURRENT PROTOCOLS IN IMMUNOLOGY 1993.

In one embodiment, the antibody of the present invention specifically binding to human FGF19 also shows cross-reactivity with cynomolgus ortholog of human FGF19. The term "cross-reactivity" as used herein refers to the ability of an antibody to react with a homologous or orthologous protein derived from other species. The cross-reactivity of an antibody can be determined using any method as known in the art. For example, it can be determined by measurement of binding affinity via surface plasmon resonance (e.g., BIACORE) or a similar technique (e.g. KinExa or OCTET).

In some embodiments, the antibody or antigen-binding fragment of the present application does not or minimally affect FGF19-suppressed CYP7A1 expression. In other words, the CYP7A1 expression is comparably inhibited by FGF19 when administering the antibody or antigen-binding fragment. More specifically, the change, or specifically increase, of CYP7A1 expression level is no more than 5%, 10%, 15% or 20% after administering the antibody or antigen-binding fragment, in the presence of FGF19.

In some embodiments, the antibody or antigen-binding fragment of the present application does not impair or marginally impairs FGF19-maintained bile acid homeostasis. A stable bile acid homeostasis can be determined by monitoring the transcription or expression level of one or more genes involved in bile acid metabolism in relevant tissues. For example, said genes can be genes coding for bile acid transporter proteins. Specific genes to be measured can be ASBT, IBABP, CYP7A1, NTCP, OATP2, BSEP, OSTa, OSTP, MRP2, MRP3, and/or MRP4 in liver, kidney and/or ileum. The change of expression level of one or more of ASBT, IBABP, CYP7A1, NTCP, OATP2, BSEP, OSTa, OSTP, MRP2, MRP3, and/or MRP4 in liver, kidney and/or ileum is limited, for example no more than 5%, 10%, 15% or 20% after administering the antibody or antigen-binding fragment, in the presence of FGF19.

The antibody of the present application can be subjected to a purification process to remove unwanted materials, resulting in a purified antibody. Conventional methods for purifying antibodies include but not limited to column chromatography methods, which are well known in the art.

The antibody or the antigen-binding fragment of the present invention can be an isolated antibody. By the term "isolated" it means that the antibodies or antigen-binding fragments are at least partially free of other biological materials or non-biological materials from the cells, cell cultures, growth medium, expression system in which they are produced. Said materials may include nucleic acids, proteins, lipids, carbohydrates, buffer, salt or other material such as cellular debris and growth medium.

The present application also contemplates an antibody or antigen-binding fragment thereof comprising one or more conservative substitutions, as long as the antibody or antigen-binding fragment binds to FGF19 and possesses at least one of the properties of the antibody as described herein. "Conservative substitutions" of amino acids are well known in the art and generally refer to change one an amino acid residue into another amino acid residue having a similar side chain in structure or function. For example, an exemplary list of conservative substitutions are provided in the table below.

| Original amino acid residue | Conservative substitution(s) |
| --- | --- |
| Ala | Gly; Ser |
| Arg | Lys; His |
| Asn | Gln; His |
| Asp | Gln; Asn |
| Cys | Ser; Ala |
| Gln | Asn |
| Gln | Asp; Gln |
| Gly | Ala |
| His | Asn; Gln |
| Ile | Leu; Val |
| Leu | Ile; Val |
| Lys | Arg; His |
| Met | Leu; Ile; Tyr |
| Phe | Tyr; Met; Leu |
| Pro | Ala |
| Ser | Thr |
| Thr | Ser |
| Trp | Tyr; Phe |
| Tyr | Trp; Phe |
| Val | Ile; Leu |

The present application also provides an isolated nucleic acid sequence comprising a nucleotide sequence coding for the antibody or fragment thereof the present application. By "isolated nucleic acid" or "isolated polynucleotide", it means a DNA or RNA which is removed from all or a portion of a polynucleotide in which the isolated polynucleotide is found in nature, or is linked to a polynucleotide to which it is not linked in nature. An isolated nucleic acid molecule "comprising" a specific nucleotide sequence may include, in addition to the specified sequence, operably linked regulatory sequences that control expression of the coding region of the recited nucleic acid sequences. Due to the codon degeneracy, one skilled in the art can understand that a specific amino acid sequence can be coded by different nucleotide sequences.

Therapeutic Uses

The present disclosure provides a method for preventing, treating or preventing recurrence of a disease or a disorder caused by or related to abnormal FGF19-FGFR4 signaling, comprising administering to a subject in need thereof an therapeutically effective amount of the antibody or antigen-binding fragment of the first aspect of the present application, or the pharmaceutical composition of the second aspect of the present application. In a specific embodiment, the disease or disorder is cancer caused by or related to abnormal FGF19-FGFR4 signaling. In a more specific embodiment, the cancer is hepatocellular carcinoma (HCC).

The terms "administration", "administering", "treating" and "treatment" as used herein, when applied to a subject, e.g. an animal, including human, or to cells, tissue, organ, or biological fluid, mean contact of an exogenous pharmaceutical, therapeutic, diagnostic agent, or composition to the subject, cell, tissue, organ, or biological fluid. Treatment of a cell encompasses contact of a reagent to the cell, as well as contact of a reagent to a fluid, where the fluid is in contact with the cell. The term "administration" and "treatment" also include in vitro and ex vivo treatments, e.g., of a cell, by a reagent, diagnostic, binding compound, or by another cell.

The term "therapeutically effective amount" as used herein, refers to the amount of an antibody that, when administered to a subject for treating a disease, or at least one of the clinical symptoms of a disease or disorder, is sufficient to effect such treatment for the disease, disorder, or symptom. The "therapeutically effective amount" can vary with the antibody, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

In the context of the present application, by "subject" it refers to an animal, preferably a mammal, e.g., a primate, preferably a higher primate, e.g., a human.

The terms "cancer" or "tumor" herein mean or describe the physiological condition in mammals that is typically characterized by unregulated cell growth. In a preferred embodiment, the cancer is related to aberrant FGF19-FGFR4 signaling. The antibody or the antigen-binding fragment of the present application can be contemplated that the anti-FGF19 antibody of the present application can be used to treat, for example, breast cancer, prostate cancer, colon cancer, lung cancer, and gastric cancer.

EXAMPLES

Materials and Methods

The following materials and methods are used in the Examples.
Cell Lines

The human hepatocellular carcinoma cell line Hep3B was a kind gift from Dr. Fengming Lu's lab in the Peking University Health Science Center. Hep3B cells were cultured in DMEM medium supplemented with 10% fetal bovine serum (Gibco, DMEM, C11965500BT). Cells were cultured in a humidified incubator at 37° C. with a 5% $CO_2$ atmosphere.

The Hep3B-Luc23 stable cell line expressing firefly luciferase reporter gene was generated through lentivirus transduction and selected with puromycin.

The FreeStyle 293-F cell line was cultured in FreeStyle™ 293 Expression Medium (both the cell line and the medium are from Thermal Fisher Scientific) in a humidified orbital shaker platform at 37° C. with an 8% $CO_2$ atmosphere.
Expression and Purification of Proteins For human FGF19 (SEQ ID NO: 1) and its variants, including the N-terminus deletion variant FGF19$^{\Delta NT}$ (having an amino acid sequence corresponding to residues Arg43-Lys216 of SEQ ID NO: 1) and the FGF19 alanine substitution mutants, the coding sequences for the proteins were cloned into a mammalian cell expression vector with a C-terminal His-Avi tag and these were transiently transfected alone or co-transfected with an expression vector encoding protein sequence of E. coli BirA biotin-protein ligase into FreeStyle 293-F Cell (Thermal Fisher Scientific) at a 1:1 ratio. At 3-5 days after transfection, cell supernatants were collected and proteins or biotinylated proteins were purified using Ni-NTA affinity chromatography (QIAGEN).

For full-length human IgG1 antibody production, the coding sequences of the VH and VL were cloned, respectively, into a human IgG1 heavy chain (HC) mammalian cell expression vector and a light chain (LC) mammalian cell expression vector. FreeStyle 293-F Cells were co-transfected transiently with the two expression plasmids (HC and LC plasmids) at a 1:1 ratio. At 3-5 days after transfection, cell culture supernatant was collected for purification of human IgG1 antibody using affinity chromatography with Protein A beads (GE Healthcare Life Sciences).
Screening of Antibody Library Against FGF19

An FGF19 N-terminal peptide (SEQ ID NO: 24), comprised of residues Arg23 to Ile42 of FGF19 N-terminus followed by 5 amino acids (SGSGK) with a biotin modification at its C-terminus, was synthesized by Scilight-peptide (Beijing, China) with purity greater than 95%. The N-terminus FGF19 peptide or the biotinylated full-length FGF19 protein was captured as target protein on streptavidin-conjugated magnetic M-280 Dynabeads® (Thermal Fisher Scientific) and then incubated with $5 \times 10^{12}$ phage-scFv (single-chain fragment of variable domain) particles prepared from a human non-immune antibody phage display library constructed from peripheral blood mononuclear cells of 93 healthy donors (size: $1.0 \times 10^{10}$). Two rounds of selection were performed. For the second round of selection, a decreased amount of target protein was used and extensive washing steps were applied. A conventional basic triethanolamine solution was used to elute phages exhibiting specific binding to the target protein.

Subsequently, single clones were picked and rescued to produce phage-scFvs in the bacterial culture supernatant; these were screened for specific binding to the N-terminus of FGF19 in an enzyme-linked immunosorbent assay (ELISA) by comparing the binding to full length FGF19 and N-terminus deleted version of FGF19 (FGF19$^{\Delta NT}$). Clones that bound to FGF19 with higher affinity than FGF19$^{\Delta NT}$ were selected as candidates having specific binding to N-terminus of FGF19, and the genes of variable regions of the heavy (VH) and light (VL) chains of these clones were sequenced. Corresponding amino acid sequences of the selected clones were aligned to eliminate repeated clones and to thereby identify unique antibodies for further characterization.
31A3 Antibody Sub-Library Construction and Selection for Affinity Improvement To improve the affinity of antibody 31A3 via CDR3-targeted randomization, a sub-library with random mutagenesis for the HCDR3 and LCDR3 of 31A3 was constructed through NNK degenerate codons. The size of the constructed antibody sub-library was $1.23 \times 10^8$. Antibody sub-library selection and screening were done similarly as described above for screening of antibody library against FGF19. To obtain high-affinity hits from the magnetic beads, competitive elution with 31A3 hIgG1 was used. Subsequently, single clones were picked and rescued to produce phage-scFvs in the bacterial culture supernatant to screen for binding to FGF19. Only hits with higher binding affinities than 31A3 were retained.

ELISA Assay

2 μg/mL of NeutrAvidin (Sigma Aldrich) in phosphate buffered saline (PBS) was coated onto 96-well U-bottom plate (Nunc, MaxiSorp™) at 100 μL per well and incubated at 4° C. overnight. 2 μg/mL of biotinylated FGF19 or FGF19 variants at 100 μL per well were then captured onto the plates by incubation at 30° C. for 0.5-1 hour. FGF19 or FGF19 variants were also coated onto 96-well U-bottom plate directly at 100 μL per well and incubated at 4° C. overnight. For hIgG1 antibody based ELISA, three-fold serially diluted antibodies in PBS containing 2% non-fat milk were added at 100 μL per well. For competition ELISA, tested antibodies were in three-fold serial dilution and mixed with competitor FGFR4-hFc. Bound antibodies were then detected using an HRP-conjugated goat anti-hFc antibody (Thermo Fisher Scientific).

Binding Kinetic Analysis by Surface Plasmon Resonance Analysis (SPR) Assay

Kinetic analysis of the anti-FGF19 human IgG1 antibodies of the present application was performed using a Biacore T200 system (GE Healthcare Life Sciences) at 25° C. Anti-hFc antibody (GE Healthcare Life Sciences) was immobilized on a CM5 sensor chip using an amine-coupling kit (GE Healthcare Life Sciences). The anti-FGF19 human IgG1 antibodies of the present application were captured as a ligand on the sensor chip with subsequently injection of analyte FGF19 (at 2-fold serial dilution from 100 nM) or FGF19 alanine mutants (50 nM) to each flow cell. Injection of buffer (HBS with 0.5% Tween20 and 0.3 mM EDTA) was served as a negative control. 3M $MgCl_2$ was used as regeneration buffer between each association and dissociation cycle. The association rates (ka), dissociation rates (kd), and affinity constants (KD) were calculated using BiacoreT200 evaluation software.

Cell Proliferation Assay

The human HCC cell line Hep3B was treated with different concentrations of FGF19 or FGF19 variants in DMEM supplemented with 1% fetal bovine serum to induce excessive cell proliferation. For evaluation of inhibition activity against FGF19-induced cell proliferation by anti-FGF19 antibodies, 15 μg/ml (100 nM) hIgG1 antibody was added to cell culture medium. 72 hours later, cell proliferation was measured using Cell Counting Kit-8 (Dojindo Molecular Technologies) according to the product instructions of the manufacturer.

Expression of CYP7A1 in Liver 5-6 week-old C57BL/6 mice were fasted overnight before intraperitoneal (i.p.) injection of 2 μg (1) FGF19, (2) FGF19 variants, or (3) FGF19 together with 60 μg anti-FGF19 antibodies. Mice were euthanized 3 hours after i.p. injection and livers were harvested. For subsequent analysis of CYP7A1 mRNA expression levels, total RNA of livers was extracted using TRIzol reagent (Thermo Fisher Scientific) and complementary DNA (cDNA) was generated by reverse transcription using a Prime Script RT-PCR Kit (Takara). The CYP7A1 mRNA expression level (relative to GAPDH) was evaluated by qPCR with an ABI Fast 7500 real time instrument (Applied Biosystems).

Animal Experiments

NOD SCID and NSG mice were used for evaluating the anti-tumor activity of anti-FGF19 antibodies. 6-8 week-old mice were subcutaneously injected with $5 \times 10^6$ Hep3B cells (100 μl per mouse) in the right flank. Mice were divided into three groups (n=6 per group) based on equivalent mean tumor bioluminescence intensities or tumor volumes, and received intraperitoneal (i.p.) injection of 200 μg G1A8 or control IgG twice a week. In vivo tumor bioluminescence intensities of tumor-bearing mice were measured using an IVIS Lumina III In Vivo Imaging System (PerkinElmer) after i.p. injection of 15 mg/kg D-luciferin (PerkinElmer). Tumor volume was measured with an electronic caliper and calculated using the formula $3.14 \times L \times W^2/6$, where L and W are the largest and smallest measured diameters, respectively. All animal protocols were conducted by following the National Guidelines for Housing and Care of Laboratory Animals in China and performed in accordance with institutional regulations after approval by the IACUC at NIBS. The study to evaluate anti-tumor efficacy of antibodies in patient-derived xenograft in BALB/c Nude mice was conducted under approved IACUC protocols at Crown Bioscience Inc.

Safety assessment of the antibody of the present application, specifically G1A8, was conducted in JOINN Laboratories (Beijing), Inc. 3-4 year-old healthy naïve cynomolgus monkeys weighing ~3 kg were intravenously injected with G1A8 antibody in an amount of 30 mg/kg body weight or saline as a control at day 16 in an amount of 30 mg/kg body weight. Clinical observations, body weight, body temperature, blood chemistry, and anatomic pathology were assessed. Blood samples were collected at various time points (day −1, day 8, day 15, day 23 and day 30) for pharmacokinetic analysis of G1A8. Liver, ileum, and kidney samples were collected at the end of the study for RNA analysis of genes related to bile acid metabolism.

Crystallization and Structural Determination of FGF19-G1A8 Complex

FGF19 and G1A8-Fab were separately expressed in FreeStyle 293-F cells and individually purified by Ni-NTA flow chromatography (QIAGEN). To obtain the FGF19-G1A8 complex, FGF19 and G1A8-Fab were mixed in a 1:1 molar ratio, incubated at 4° C. overnight and further purified by a Superdex S200 10/300 column (GE Healthcare) with buffer containing 10 mM Tris-HCl pH 8.0 and 500 mM NaCl. The purified FGF19-G1A8 complex was then concentrated to 18 mg/mL and crystallized at 20° C. using the hanging-drop vapor diffusion method by mixing 1 μL of protein and 1 μL of reservoir solution containing 0.2M Lithium Sulfate monohydrate, 0.1M Bis-Tris pH 6.9, 26% w/v Polyethylene Glycol 3350. Quadrilateral-shape crystals appeared in 7 days. The crystals were flash-frozen in liquid nitrogen.

X-ray diffraction data were collected at the Shanghai Synchrotron Radiation Facility (SSRF) beamline BL17U. Data were processed in HKL2000 and XDS. Crystals belong to the $P2_12_12_1$ space group and contain two copies of FGF19-G1A8 complex per asymmetric unit. Structure was determined by molecular replacement using Phaser in Phenix with the following structures as search models: FGF19 (PDB ID: 2P23) and anti-steroid Fab 5F2 structure (PDB ID: 3KDM). The model was iteratively built in Coot and refined in PHENIX.

Statistical Analysis

All analyses were performed using GraphPad Prism version 6.00. Ordinary one-way ANOVA or unpaired Student's t-tests were used for comparisons between groups. Two-way ANOVA and Turkey's multiple comparison tests were used to assess continuous variables. Kaplan-Meier survival analysis and log-rank tests were used for survival analysis.

Example 1. Identification of Binding Target at N-Terminus of FGF19

The present inventors performed a variety of assays to investigate whether functional difference exits between full-length FGF19 and its N-terminus deletion version.

It was found that, compared to full-length FGF19, a FGF19$^{\Delta NT}$ variant (FGF19$^{\Delta NT}$ having an amino acid sequence corresponding to residues Arg43-Lys216 of SEQ ID NO: 1) had significantly weaker binding affinity for FGFR4 and exerted significantly reduced activity to induce tumor cell proliferation in an in vitro assay (FIGS. 1A and B).

Further, the bile-acid-regulatory function of full-length FGF19 and said N-terminus deletion variant FGF19$^{\Delta NT}$ was tested. A mouse model was used in this test since it was found that exogenous FGF19 could exert its bile-acid-regulatory function through binding to the murine receptor FGFR4 that shares 90% amino acid identity with human FGFR4, to repress the murine hepatic transcription of CYP7A1 (M. Zhou et al., 2014, supra; R. Goetz et al., *Molecular and cellular biology* 27, 3417-3428 (2007)). After intraperitoneal injection of FGF19 or FGF19$^{\Delta NT}$ the hepatic CYP7A1 gene expression levels in these mice were assessed. No statistically significant difference was observed between the full-length and the N-terminus deletion variant FGF19$^{\Delta NT}$ in bile-acid-regulatory function through repression of hepatic CYP7A1 gene expression level (FIG. 1C). In light of these results, it can be reasonably expected that a therapeutic agent which targets the N-terminus of FGF19 could potentially inhibit its tumorigenic activity without deleteriously affecting its bile-acid-regulatory physiological function.

Example 2. Generation of Antibodies Specifically Targeting N-Terminus of Human FGF19

Figure 2:
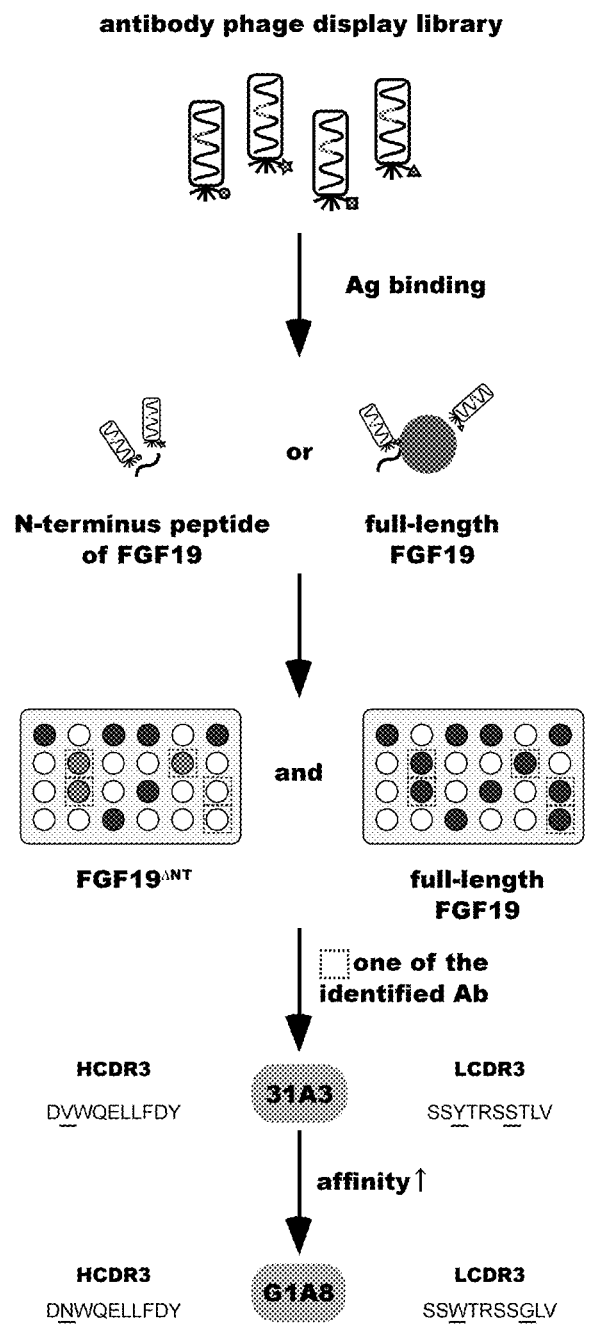
FIG. 2 is a schematic diagram which illustrates the generation of antibody G1A8 using the antibody phage display technology. The N-terminus peptide of FGF19 or the full-length FGF19 protein was used as antigen to select against the inventors' large non-immune antibody phage display library (D. Li et al., A potent human neutralizing antibody Fc-dependently reduces established HBV infections. Elife 6, (2017)). Through subsequent ELISA screening with both full-length FGF19 and N-terminus deletion variant FGF19$^{\Delta NT}$, antibodies that bind to FGF19 with higher affinity than FGF19$^{\Delta NT}$ were identified. A well shaded with dark grey color indicates a higher affinity as compared to a well shaded with light grey color or with a white color. Protein sequences of both heavy chain and light chain CDR3 regions of one identified antibody 31A3 and its affinity improved antibody G1A8 are shown in parallel, with the different amino acids underlined.

The following two different selection strategies, using either SEQ ID NO: 1 or SEQ ID NO: 24 as binding target, were designed to identify antibodies that specifically target the N-terminus of FGF19 (FIG. 2). Antibody selection was conducted by using either an FGF19 N-terminal peptide (SEQ ID NO: 24) or the full-length FGF19 (SEQ ID NO: 1) as the binding target and a large non-immune human antibody phage display library (D. Li et al., Elife 6, 2017, supra) was selected. Antibodies that showed binding affinity to both the N-terminal fragment of FGF19 and the full-length FGF19 were selected for next step of screening.

Figure 3:
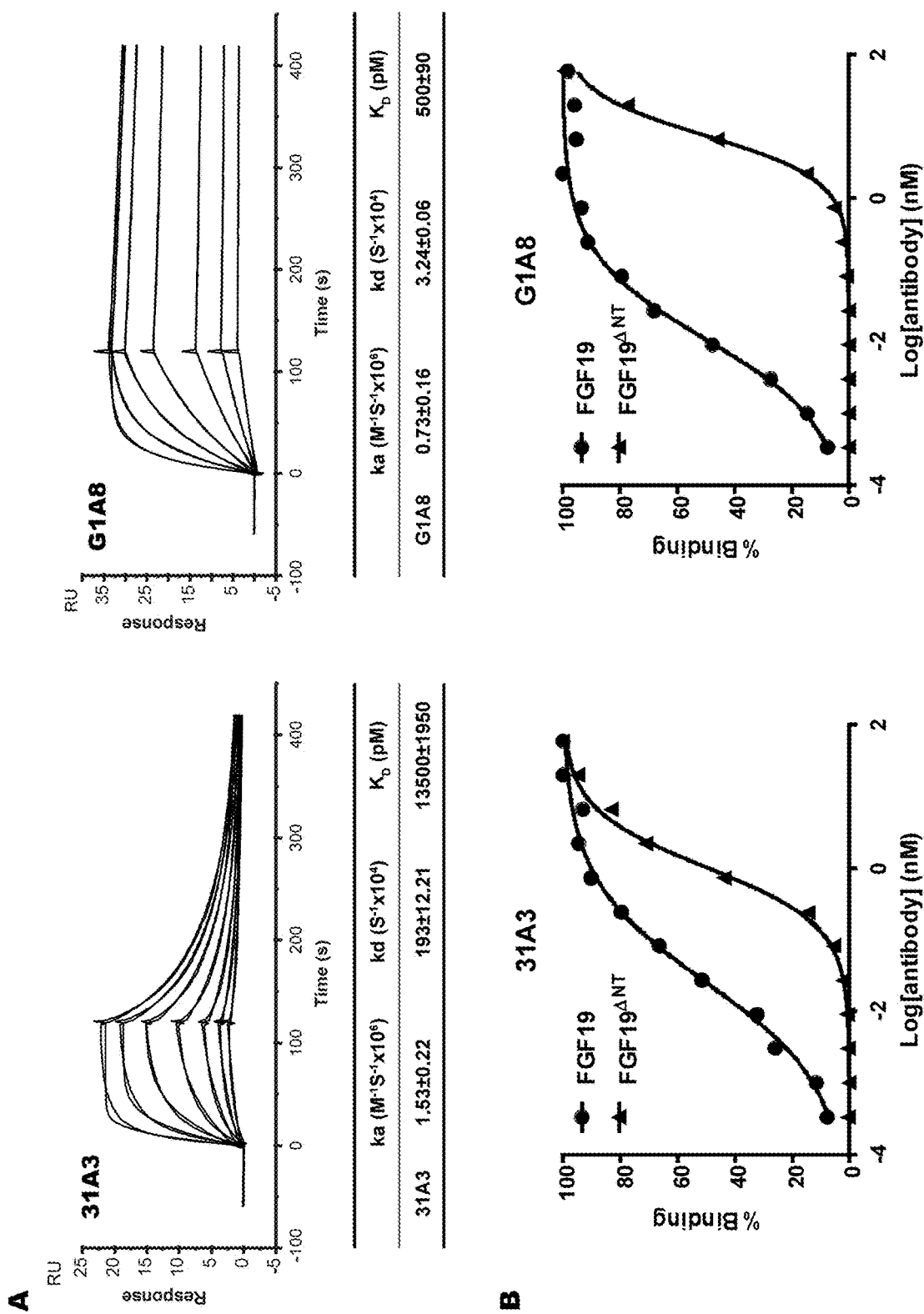
FIG. 3A-B Improved binding affinity and higher N-terminus-dependency of G1A8. (A) Kinetic analysis of the binding of anti-FGF19 antibodies 31A3 or G1A8 to FGF19 using SPR. FGF19 was in two-fold serial dilutions from 100 nM. (B) The binding of both 31A3 and G1A8 to FGF19 depends on the N-terminus of FGF19, which is shown by the different binding profile when using FGF19 or FGF19$^{\Delta NT}$ as the target. The binding activity of antibodies to FGF19 and FGF19$^{\Delta NT}$ was analyzed by ELISA.

In the following screening step using ELISA assay, both the full-length FGF19 and the N-terminus deletion variant FGF19$^{\Delta NT}$ were used as the binding target to identify antibodies that could bind to the full-length FGF19 but could not or weakly bind to the FGF19$^{\Delta NT}$. Among a number of identified antibodies, an antibody designated as 31A3 which showed relatively high binding affinity and specifically recognized the N-terminus of FGF19 was chosen for further analysis (FIGS. 2 and 3).

Example 3. In Vitro Evaluation of the Inhibitory Effect of 31A3 on Tumorigenic Activity of FGF19

Figure 4:
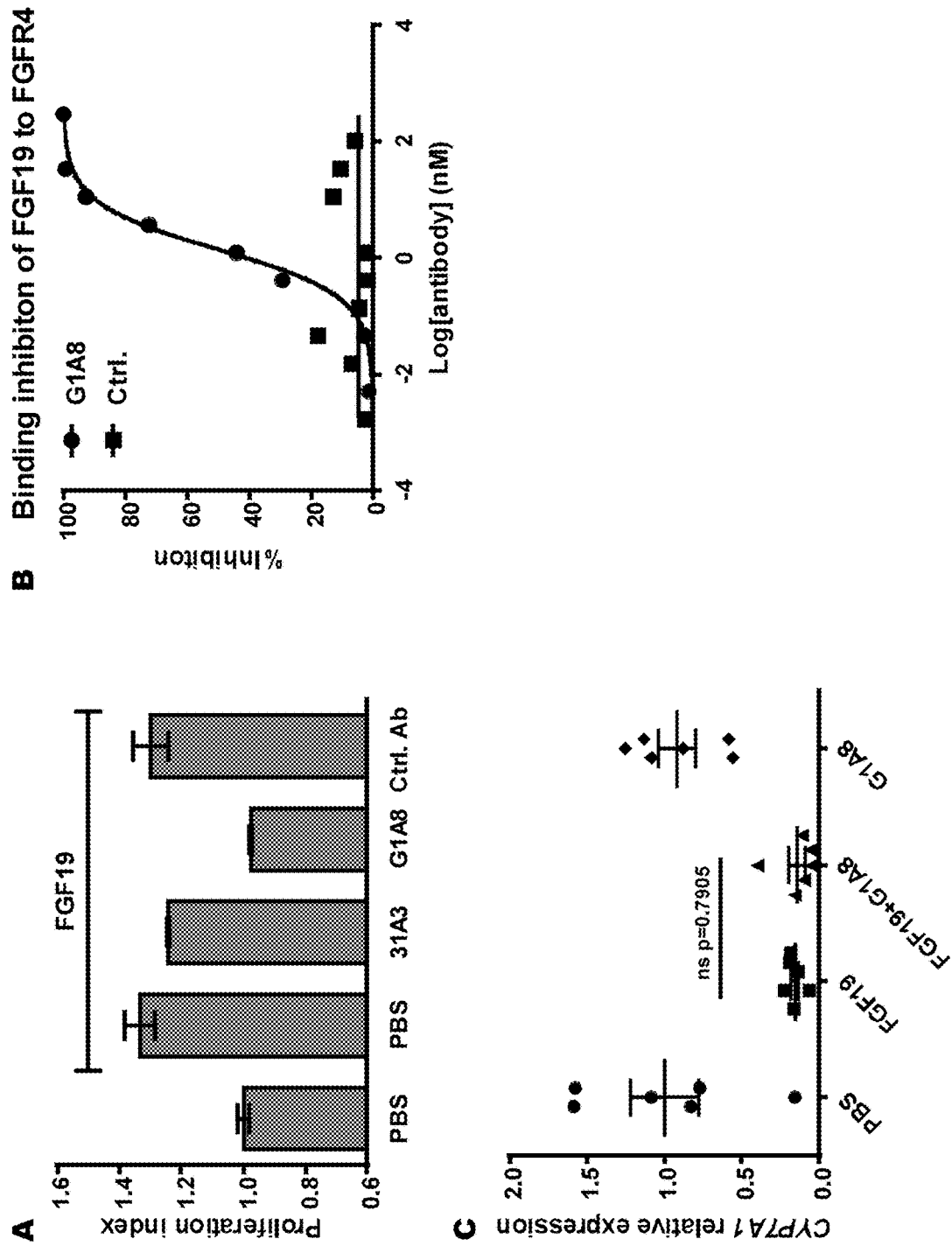
FIG. 4A-C Characterization of G1A8. (A) G1A8 and 31A3 showed inhibition of FGF19-induced cell proliferation. Hep3B was cultured with 20 ng/ml FGF19 and 100 nM anti-FGF19 antibodies or isotype control antibody. (B) G1A8 inhibited interaction between FGF19 and FGFR4. Antibody G1A8 and isotype control antibody were mixed with 100 nM FGFR4-Fc and 20 μg/ml Heparin. Binding inhibition of FGFR4 to FGF19 was analyzed by ELISA. (C) G1A8 did not impair mouse hepatic CYP7A1 gene expression down-regulated by FGF19. C57BL/6 mice were fasted before intraperitoneal injection with indicated treatments. Hepatic CYP7A1 gene expression level was analyzed by qPCR. Each group consisted of 3 male and 3 female mice. FGF19, 0.1 mg/kg; G1A8, 5-fold molar excess of FGF19.

Anti-proliferation assays were conducted to evaluate 31A3's ability to inhibit FGF19's tumorigenic activity in vitro. In order to evaluate if 31A3 can inhibit HCC cell proliferation specifically induced by FGF19, an HCC cell line Hep3B was treated with 31A3 in the presence of exogenous FGF19. As shown by FIG. 4A, 31A3 inhibited FGF19-induced proliferation of Hep3B cells.

Example 4. Creation of 31A3 Derived Mutants with Improved Binding Affinity

To improve the affinity of 31A3 for FGF19's N-terminus, site-directed alanine scanning mutagenesis was performed within 31A3's HCDR3 and LCDR3 regions, which indicated that four amino acid residues, namely V96 and W97 in HCDR3 and Y91 and T95 in LCDR3 could be potential candidates to improve binding affinity by substitution with other amino acids. The present inventors then constructed an antibody phage display library comprising 31A3-derived antibodies with randomized mutations at the above four positions within their HCDR3 and LCDR3 regions. During this 31A3-derived sub-library selection, 31A3-hIgG1 protein was used as a competitor to screen out binders with higher binding affinity to FGF19. After a stringent bio-panning selection step, a small panel of affinity-improved antibodies was obtained. One of the resulting antibodies, G1A8, in which three amino acids are different from 31A3, exhibited a 27-fold affinity increase and a 60-fold slower dissociation rate and more potent anti-proliferation activity than the parental antibody 31A3 (FIG. 2, FIGS. 3A-B, and FIG. 4A).

Figure 8:
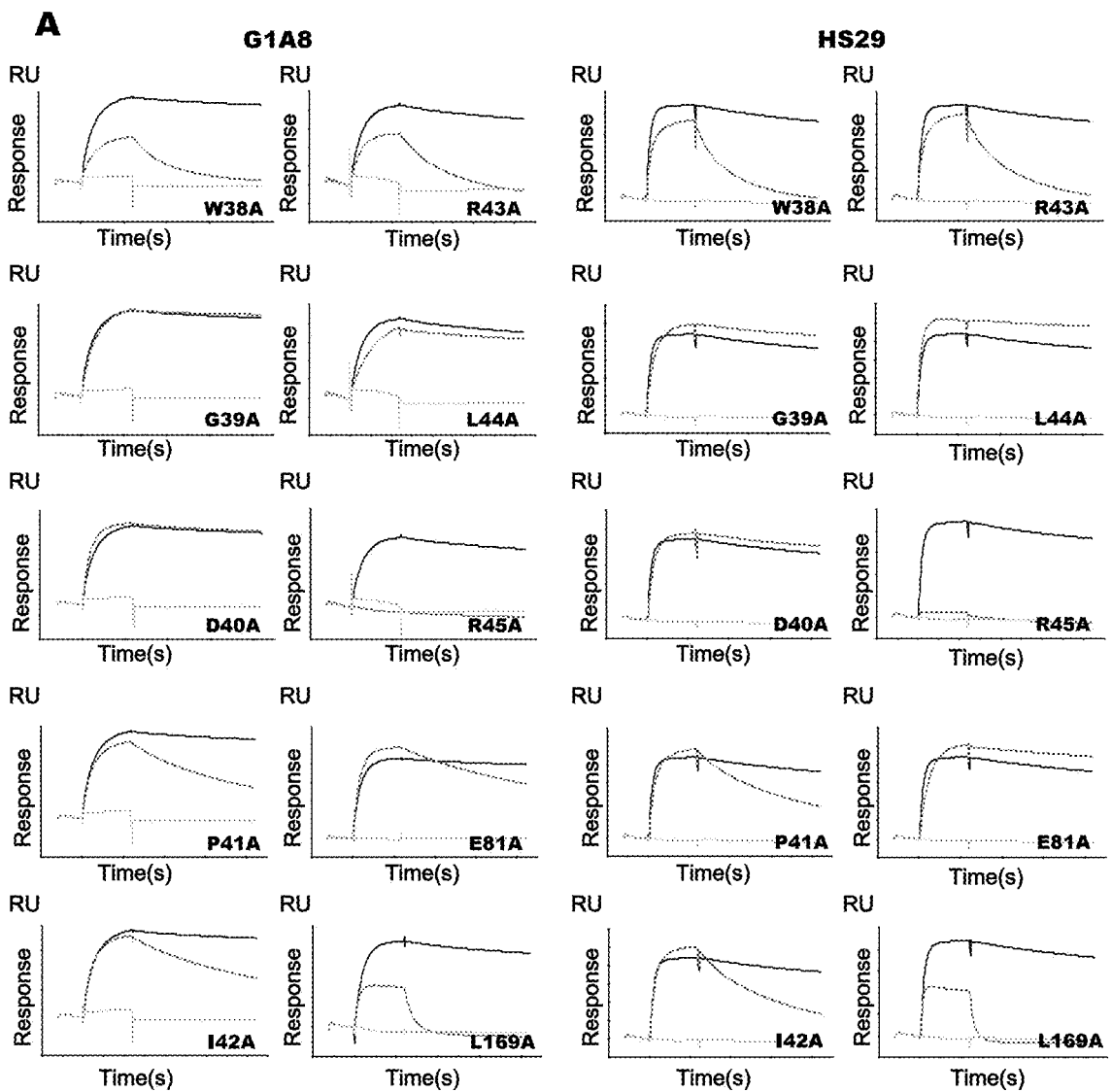
FIG. 8A-C Activities of HS29. (A) Binding analysis between anti-FGF19 antibodies G1A8 and HS29 to FGF19 alanine mutants was conducted using SPR. FGF19 alanine mutants were tested in 50 nM. (B) Kinetic analysis of the binding of HS29 to FGF19. FGF19 was in two-fold serial dilutions from 100 nM. (C) Inhibition of FGF19-induced cell proliferation by HS29. Hep3B was cultured with 20 ng/ml FGF19 and 100 nM anti-FGF19 antibodies or isotype control antibodies.
Figure 8:
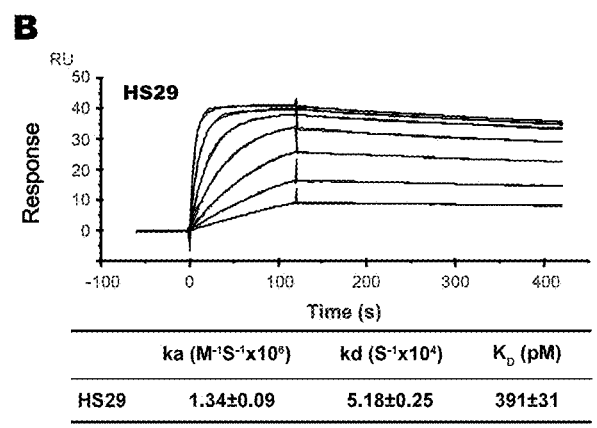
Figure 8:
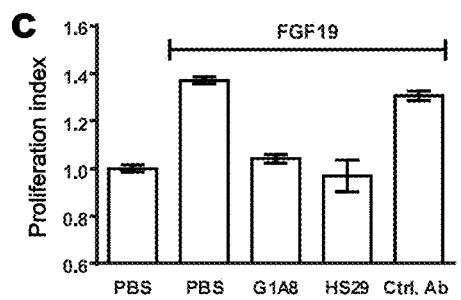

Another variant antibody HS29 was created based on the sequence analysis of the small panel of antibodies obtained from the panning. HS29 has similar binding epitope, anti-proliferation activity, and binding affinity as G1A8 (FIG. 8).

Example 5 In Vitro and In Vivo Efficacy

In in vitro studies of activity, G1A8 blocked the FGF19-FGFR4 interaction, with IC$_{50}$ values of 1.39 nM (FIG. 4B). Additionally, G1A8 also exerted a strong anti-proliferative effect with exogenous-FGF19-treated Hep3B cells (FIG. 4A).

Figure 5:
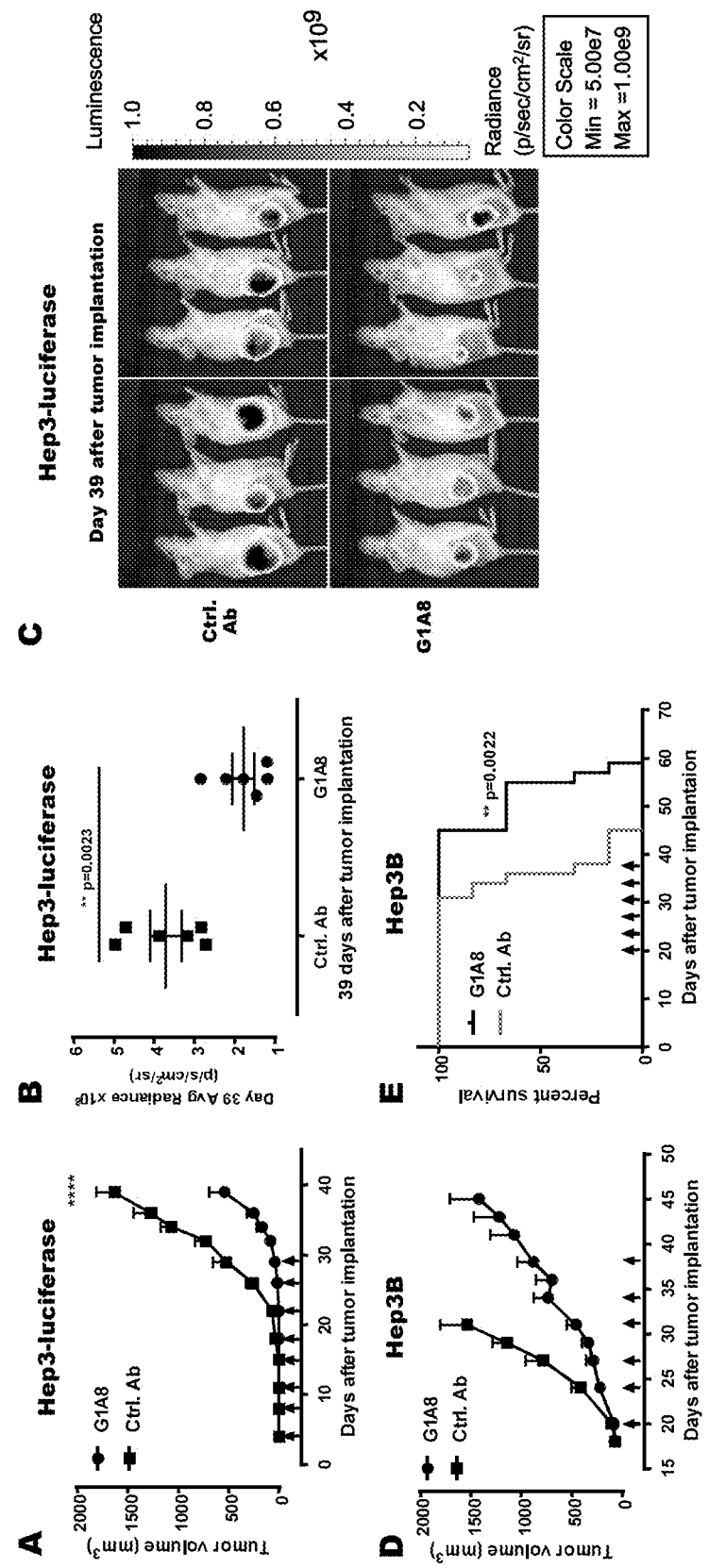
FIG. 5A-E Anti-tumor activity of G1A8 in human hepatocellular carcinoma xenograft mouse models. (A-C) G1A8 inhibited tumor growth in the early stage of tumor development. Hep3B-luciferase stably expressing luciferase was subcutaneously (s.c.) injected into NOD SCID mice. Mice were divided into groups (n=6/group) with equivalent mean tumor bioluminescence intensity and received treatment of 200 μg G1A8 or isotype control antibody. Tumor growth was measured by caliper (A), and bioluminescence (B and C). (D-E) G1A8 inhibited tumor growth in the late stage of tumor development. Hep3B (s.c.) tumor-bearing NSG mice were divided into groups (n=6/group) with equivalent mean tumor volume and received treatment of 200 μg G1A8 or isotype control antibody. Tumor growth was measured by caliper (D), and survival was analyzed by Kaplan-Meier survival analysis (E). Days on which antibody treatment was administered are marked by arrows.

Its anti-tumor activity in vivo was then evaluated using xenograft mouse models (FIG. 5). The present inventors first established a Hep3B-Luc23 cell line that stably expresses luciferase and thus enabled quantification of tumor growth using in vivo bioluminescence imaging. Mice were subcutaneously injected with these Hep3B-Luc23 cells in the right flank, and then were divided into three groups with equivalent mean tumor bioluminescence intensities prior to receiving intraperitoneal injections of the antibody treatment (200 µg of G1A8 or isotype control) twice each week for four weeks. Monitoring of tumor growth overtime by measuring tumor volumes and relative tumor cell bioluminescence intensities showed that G1A8 significantly suppressed tumor growth as compared to the isotype control antibody (FIGS. 5A-C).

Anti-tumor efficacy against xenograft tumors formed from transplanted wild-type Hep3B cells was also evaluated. Antibody treatment was started when tumor volumes reached about 100 mm$^3$ in size. Hep3B-bearing mice were divided into three groups with equivalent mean tumor volume and received intraperitoneal injection of antibody (200 µg G1A8 or isotype control antibody) twice each week for three weeks. As with the aforementioned results for Hep3B-Luc23 xenografts, G1A8 significantly inhibited Hep3B tumor progression (FIG. 5D). Moreover, treatment with G1A8 significantly prolonged survival in mice compared to the isotype control group (FIG. 5E).

Figure 9:
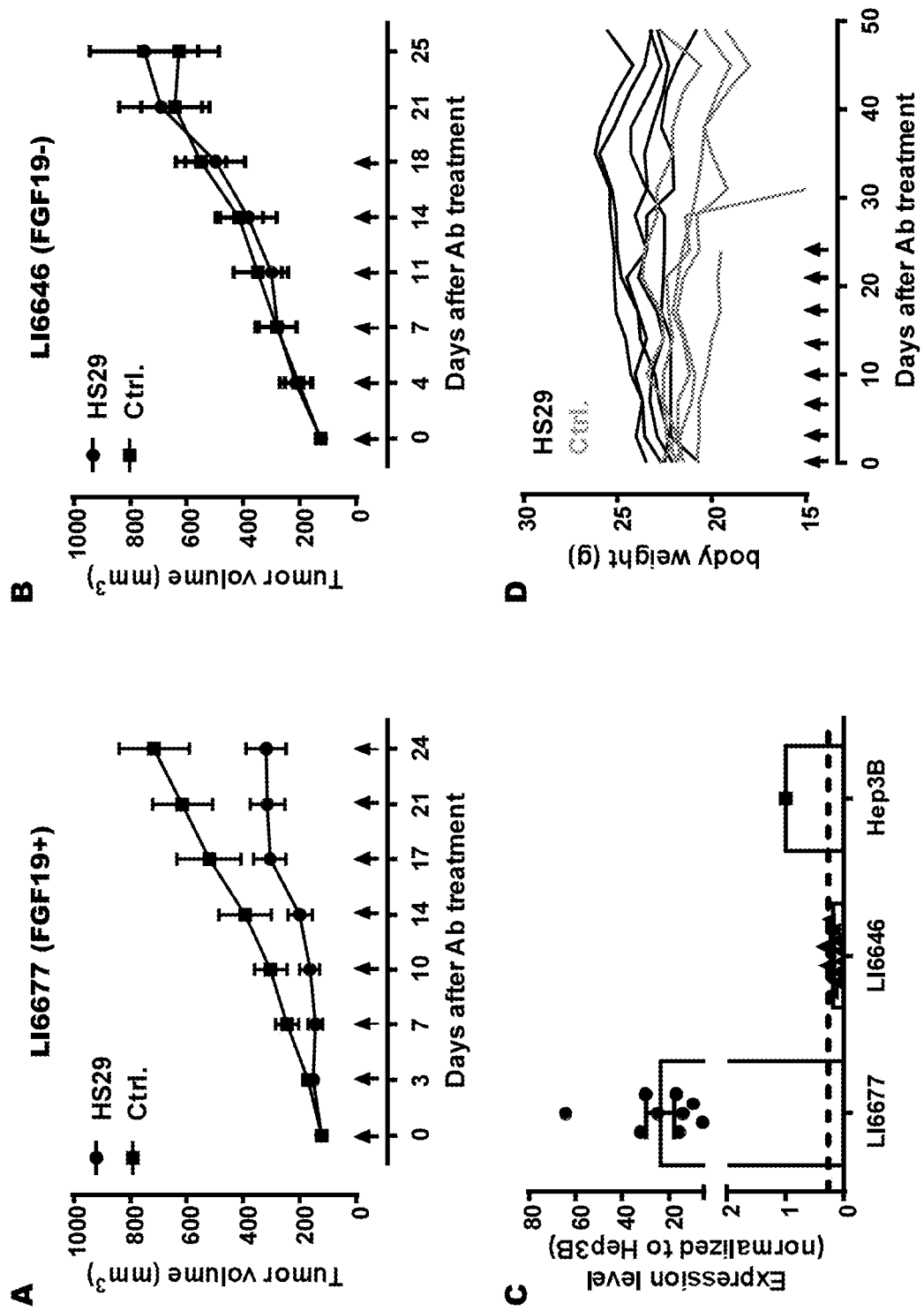
FIG. 9A-D Evaluation of anti-tumor activity of HS29 in patient-derived xenograft (PDX) models. BALB/c Nude mice bearing FGF19-expressing PDX LI6677 (A) or non-FGF19-expressing PDX LI6646 (B) were divided into groups (n=5/group) with equivalent mean tumor volume and received intraperitoneal injection of 10 mg/kg HS29 or no treatment as control. (C) FGF19mRNA expression in PDX models. Tumor samples were harvested at the end of the study and expression of FGF19 was analyzed by qPCR. Each data point represents one mouse tumor sample and the level of FGF19 mRNA expression of Hep3B culture cell line is used as a reference. The dashed line indicates the reliable detection limit of the assay. (D) Body weight of mice bearing PDX was measured during the time of study.

HS29 exhibited a strong anti-proliferation activity similar to G1A8 (FIG. 8C). The anti-tumor activity of HS29 was tested in a patient-derived xenograft (PDX) tumor model (FIG. 9A). Treatment of HS29 was started when the mean tumor volume reached approximately 150 mm³. The mice that received intraperitoneal injection of 10 mg/kg HS29 showed arrested tumor growth as compared to the control mice. Notably, control mice showed significant weight loss as tumors continued to grow and two of them died due to poor physiological conditions owing to tumor progression; whereas, HS29-treated mice maintained steady body weights and remained healthy (FIG. 9D). These data confirmed the anti-tumor activity of HS29 both in vitro and in vivo.

Example 6. Safety Assessment in Mouse and Cynomolgus Monkey

It was found that the antibody of the present application, specifically G1A8, did not show cross-reactivity with murine FGF15, the ortholog of human FGF19, which shares only 49% amino acid identity with FGF19 (T. J. Wright et al., *Dev Biol* 269, 264-275 (2004)). In view of this observation, the aforementioned mouse tumor xenograft models may not be suitable for assessing the safety profiles of G1A8 treatment. Nevertheless, recalling that human FGF19 can exert its bile-acid-regulatory function in mouse via murine FGFR4 to repress hepatic CYP7A1 transcription (M. Zhou et al., 2014, supra; R. Goetz et al., 2007, supra) (FIG. 1C), this mouse model was utilized to assess if G1A8 affects hepatic CYP7A1 transcription. It was surprisingly found that G1A8 did not affect FGF19-induced repression of hepatic CYP7A1 transcription (FIG. 4C), indicating that G1A8 does not apparently interfere with FGF19's bile-acid-regulatory function.

Previous study (Pai et al., Toxicological sciences: an official journal of the Society of Toxicology 126, 446-456 (2012)) showed that administration of the humanized anti-FGF19 antibody (1A6) in cynomolgus monkeys caused disrupted bile acid metabolism due to interrupted FGF19's function and increased CYP7A1 gene expression, with clinical manifestations of reduced body weight, low food consumption, severe diarrhea, and ultimately resulted in unscheduled euthanasia of all animals in the 10 and 30 mg/kg treatment groups. The amino acid sequence of cynomolgus monkey FGF19 and that of the human FGF19 are almost identical (sharing 98% amino acid identity). The present inventors also tested the cross-reactivity of the antibodies of the present application and verified that G1A8 bound to both cynomolgus monkey FGF19 and human FGF19 with similar binding affinities (FIG. 3A and FIG. 6L). Therefore, cynomolgus monkeys were determined to be a good model for evaluating the safety profile of G1A8, in particular if it impairs the bile-acid-regulatory function of FGF19.

Four treatment-naïve cynomolgus monkeys were randomized into two groups and received intravenous administration of control saline or 10 mg/kg G1A8 at day 1 and 30 mg/kg G1A8 at day 16. Each group included one male and one female. Blood samples were collected throughout the duration of the study (FIG. 6A).

Figure 6:
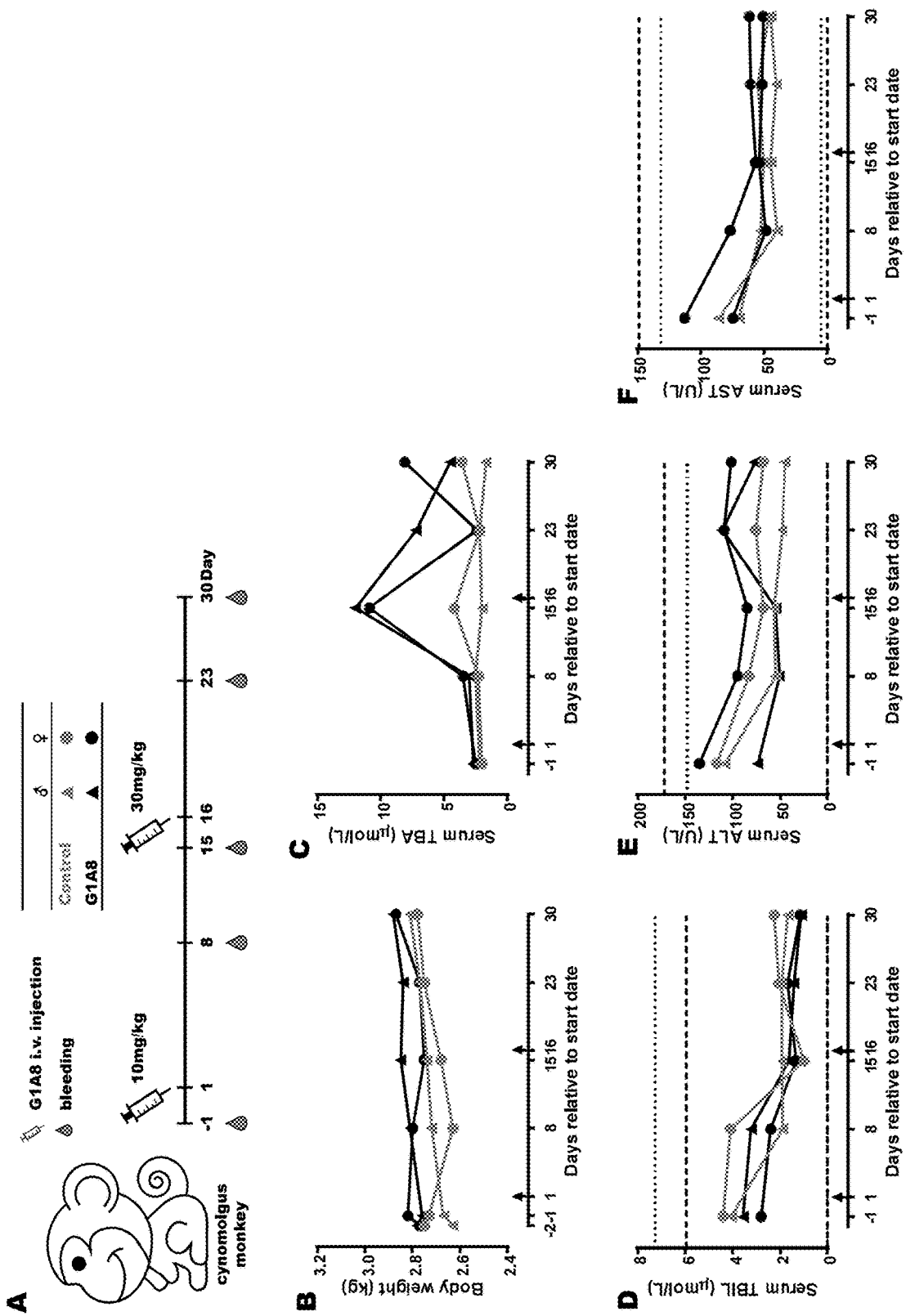
FIG. 6A-L Safety assessment of G1A8 in cynomolgus monkey. (A) Schematic diagram illustrating the timeline of G1A8 administration and sampling from animals. Four cynomolgus monkeys were divided into two groups receiving intravenous (i.v.) administration of control saline (grey) or G1A8-hIgG1 (black). Each group consisted of one male (triangle) and one female (circle) monkey. (B) Body weight of cynomolgus monkeys. (C-F) Blood biochemistry of cynomolgus monkeys. Serum TBA (C), TBIL (D), ALT (E), and AST (F) of cynomolgus monkeys were measured at various time points. Days on which intravenous administrations of G1A8 or control saline are marked with arrows. The dashed line and dotted line indicate normal reference intervals of biochemical parameters in male and female cynomolgus monkeys, respectively. (G-H) Expression of genes related to bile acid metabolism. Tissue samples of cynomolgus monkeys were harvested at the end of the study. Expression of selected genes in liver (G), ileum (H), and kidney (I) was analyzed by qPCR. (J-K) Pharmacokinetic profile of G1A8. Serum concentrations of G1A8 following administration of 10 mg/kg G1A8 on day 1 (J) or 30 mg/kg G1A8 on day 16 (K) were measured. (L) Kinetic analysis of the binding of G1A8 to cynomolgus monkey FGF19. Cynomolgus monkey FGF19 was in two-fold serial dilutions from 100 nM.
Figure 6:
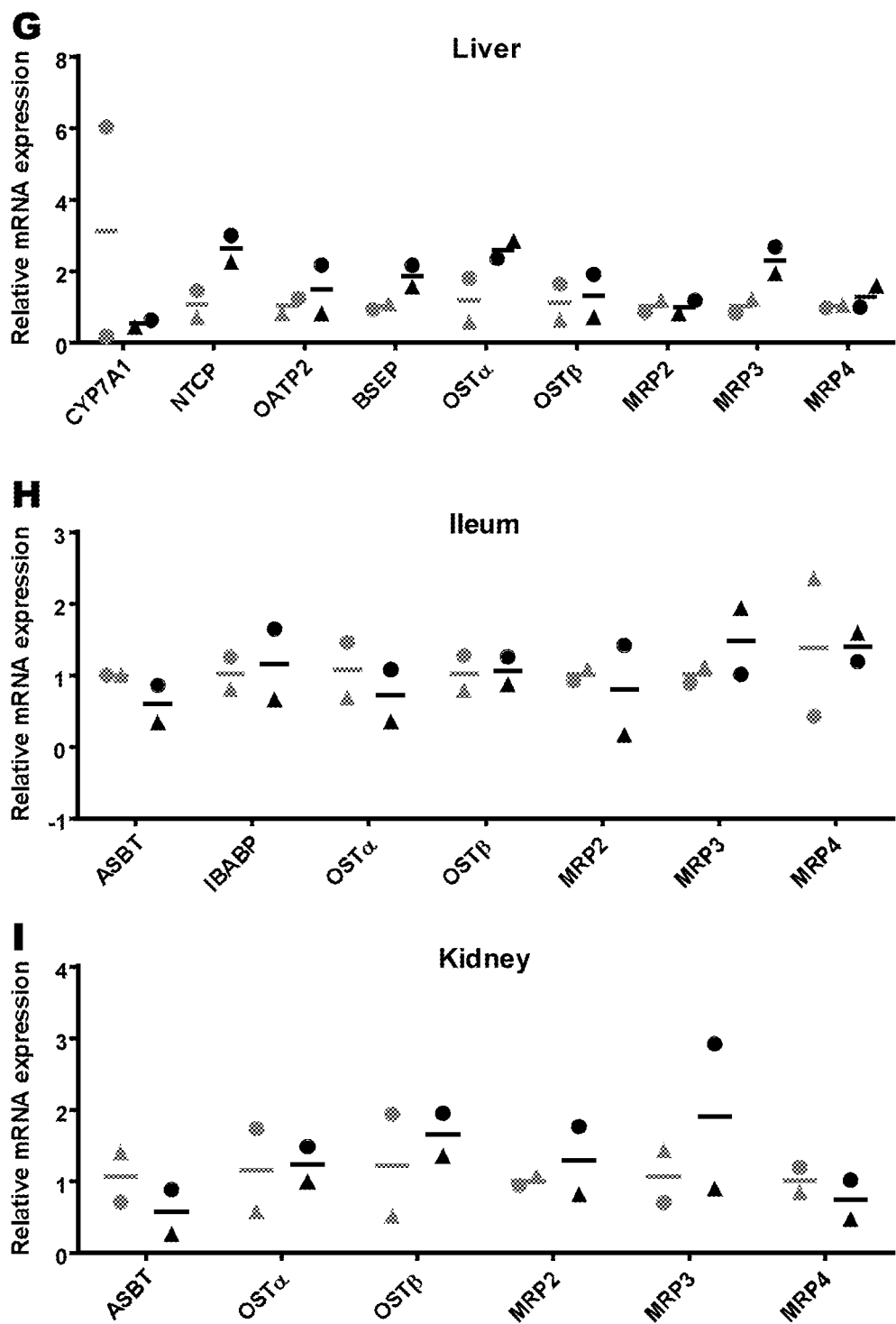
Figure 6:
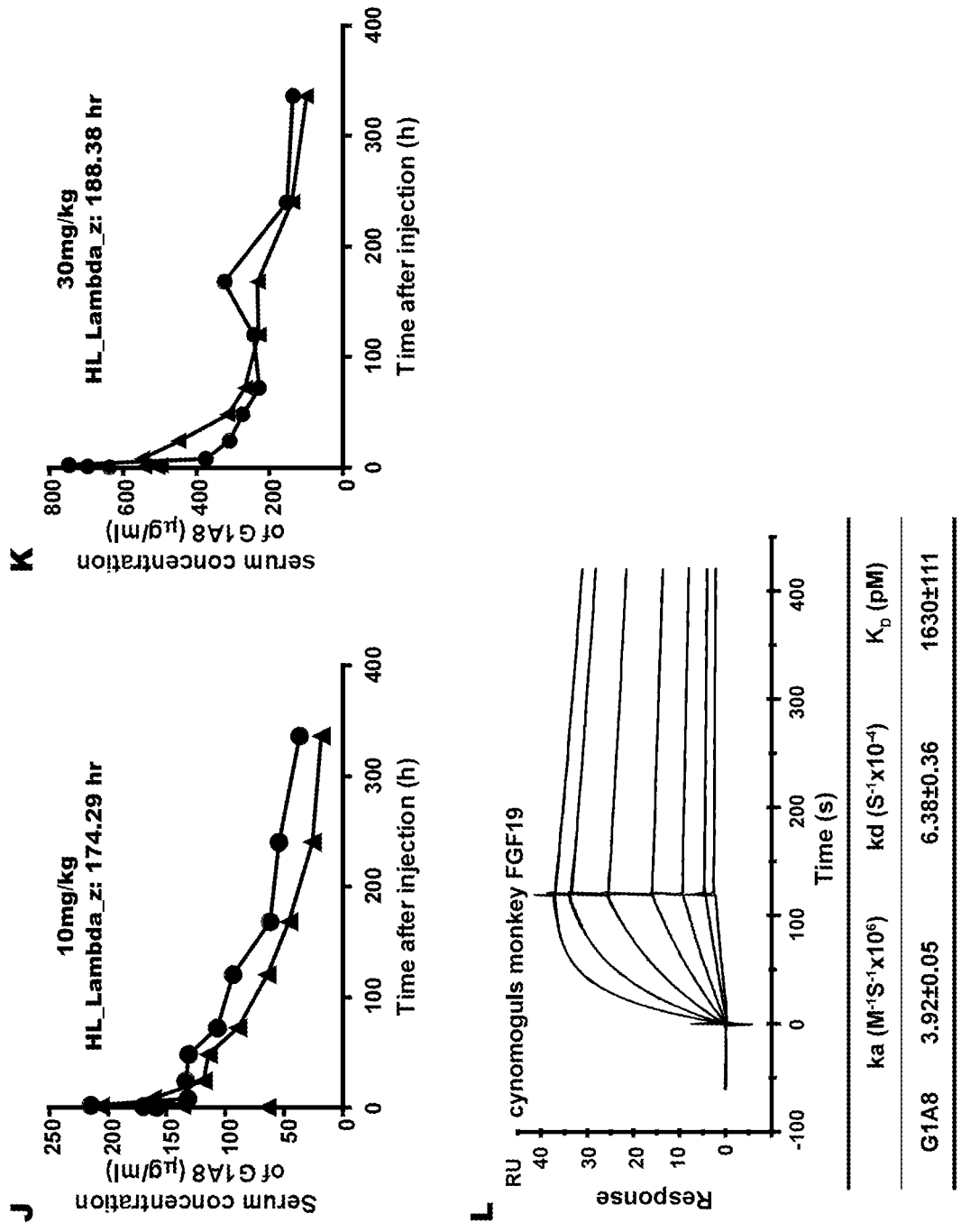

All of the monkeys completed a treatment with two doses of G1A8 administration, and none of them exhibited any of the clinical side effects that had been reported for 1A6 (which binds to the C-terminus of FGF19) including reduced body weight, low food consumption, liquid feces or diarrhea (FIG. 6B). The previous study of 1A6 treatment (a single dose) in monkeys reported a marked increase in serum total bile acid (TBA) levels, alanine transaminase (ALT), and aspartate transaminase (AST) (Pai et al., Toxicological sciences: an official journal of the Society of Toxicology 126, 446-456 (2012)). Although monkeys in the G1A8 treatment group initially showed a slight increase in serum TBA concentration at day 15 (1$^{st}$ testing time point) post G1A8 (10 mg/kg) treatment, no further increase was observed following the second administration of a higher dose of 30 mg/kg at day 16; rather a decrease was observed (FIG. 6C). This finding suggests that the slight increase in the serum TBA level observed at day 15 can likely be explained by normal physiological variations in the animals. The serum levels of total bilirubin (TBIL), alanine transaminase (ALT), and aspartate transaminase (AST) showed no significant differences in monkeys treated with either control saline or G1A8, suggesting no liver damage caused by administration of G1A8 (FIG. 6, G-I).

The present inventors also collected monkey tissue samples from the organs (liver, ileum, and kidney) that are responsible for bile acid recycling to evaluate the expression level of multiple genes known to impact bile acid metabolism (FIG. 6, D-F). In the liver of the animals treated with G1A8, no increase in CYP7A1 gene expression was found, and expression of other genes known to encode bile acid transporter proteins did not show significant increases compared to animals in the control group (FIG. 6D). In the kidney and ileum, expression of genes for bile acid transporters did not differ between the G1A8-treated group and the control group (FIGS. 6E-F), indicating that recycling and metabolism of bile acid were maintained at normal physiological level. The serum concentration-time profiles for the two different G1A8 dosages revealed a similar terminal half-life for G1A8 of 174.29 hours and 188.38 hours in cynomolgus monkeys dosed with 10 mg/kg and 30 mg/kg, respectively (FIGS. 6, J and K).

Taken together, these safety assessment experiments in cynomolgus monkey demonstrated no bile-acid-related toxicity accompanied by administration of G1A8 and thus suggest that treatment of G1A8 in a therapeutic setting is unlikely to cause significant malabsorption of bile acid or other bile-acid-related side effects.

Example 7. Structural Analysis of the FGF19-G1A8 Complex

The structure of the Fab version of G1A8 in complex with FGF19 was determined at 2.6 Å resolution by X-ray crystallography to understand the molecular basis of the interaction between the antibody of the present application and FGF19. Antibody G1A8 was selected for this analysis.

Figure 7:
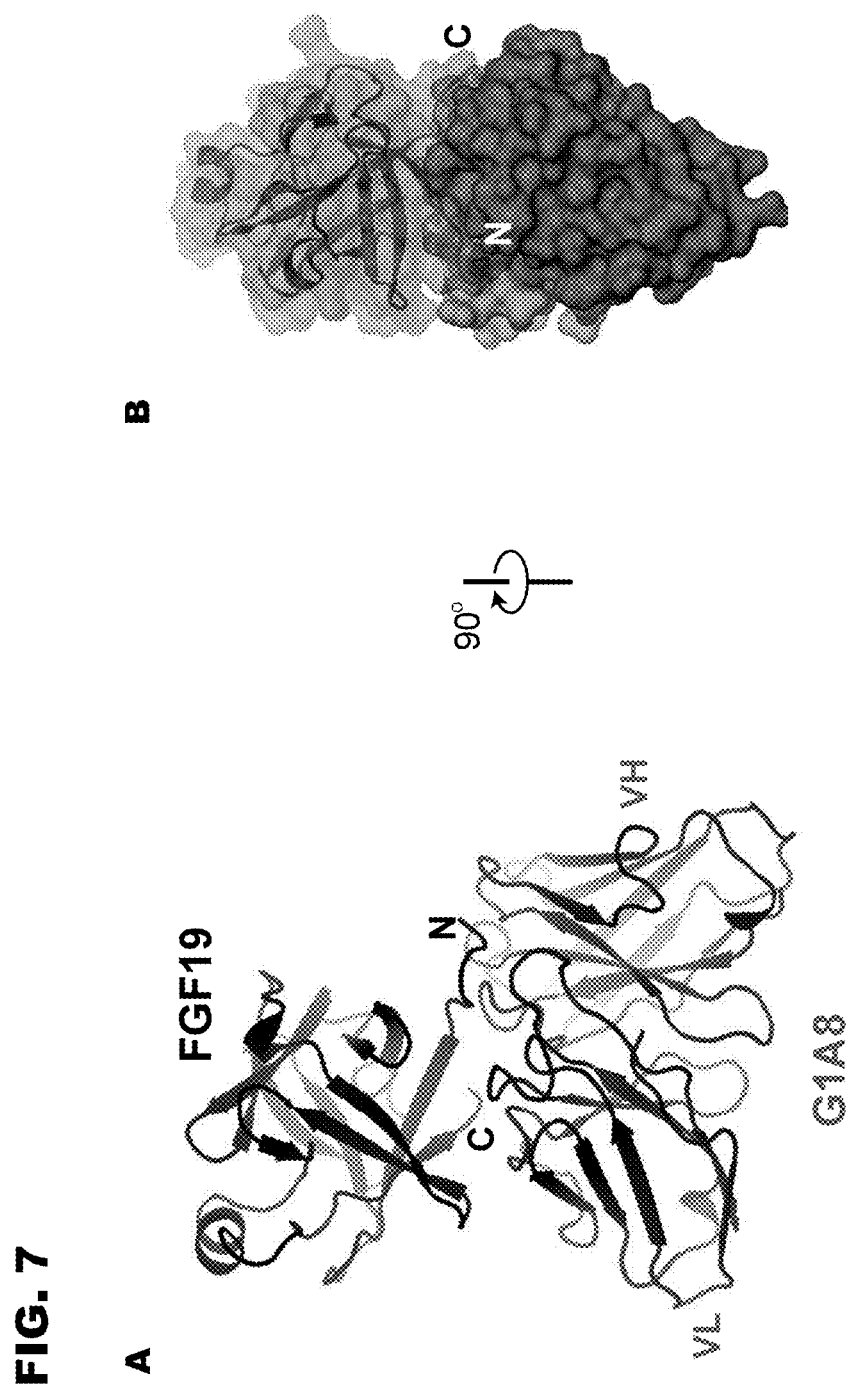
FIG. 7A-D Structural analysis of FGF19-G1A8 complex. (A) Ribbon representation of FGF19-G1A8 in orthogonal view. FGF19 is shown in black, with variable heavy chain (VH) and light chain (VL) of G1A8 in grey. The N-terminus and C-terminus of FGF19 are labeled. The constant region of G1A8 Fab is removed for clarity. (B) Surface view of the FGF19-G1A8 complex. The structure reveals apparently perfect shape complementarity. (C) The detailed view of G1A8-FGF19 interface. The dashed lines represent hydrogen bonds. (D) Binding activity of G1A8 to wild-type FGF19 and FGF19 alanine mutants in 50 nM was analyzed using SPR.
Figure 7:
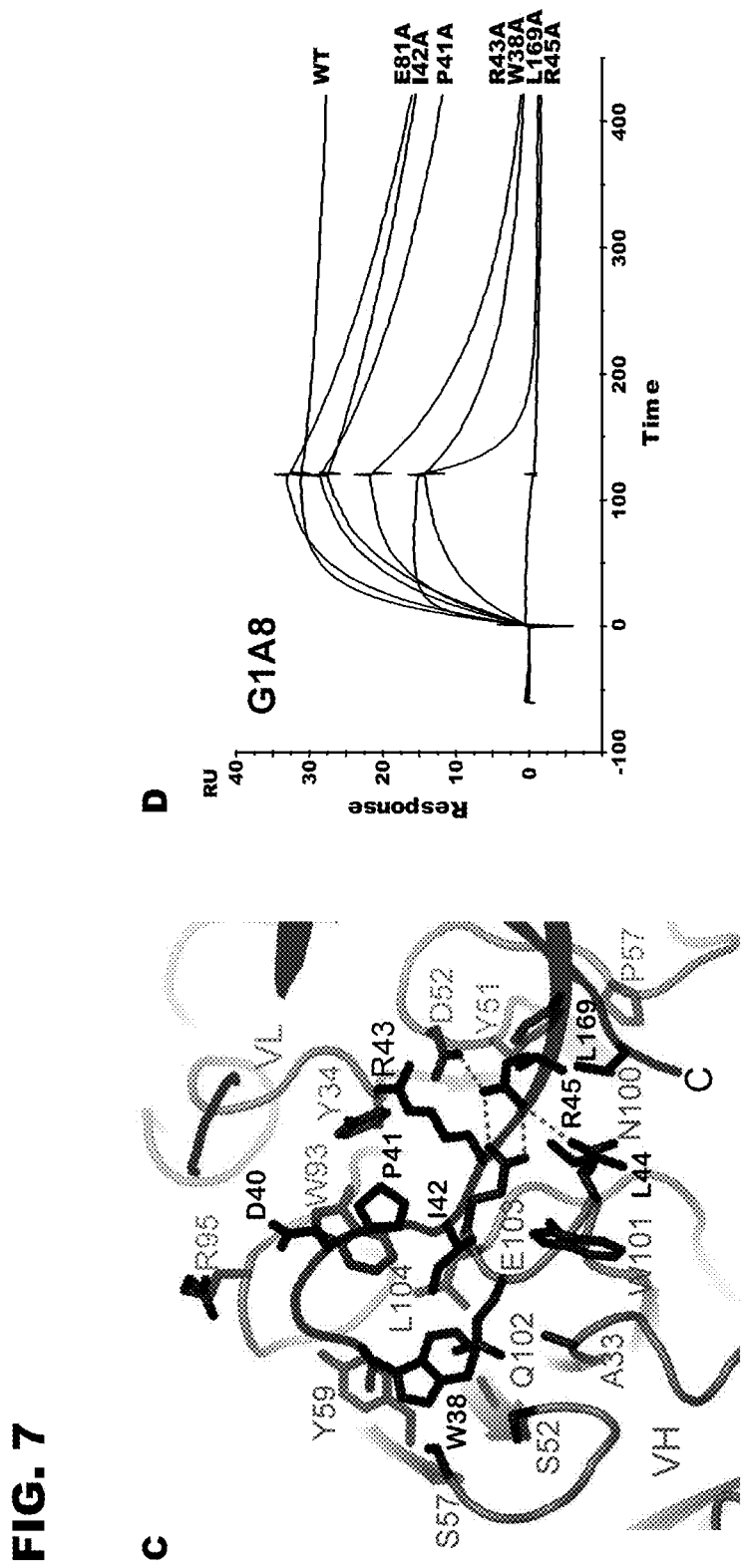

The structure was solved by molecular replacement method and refined to a $R_{work}/R_{free}$ of 0.216/0.278 with good geometry (Table 1, see below). In the structure of FGF19 and G1A8, residues 37-172 of FGF19 showing well-defined electron density were modeled. The structure of FGF19 and G1A8 shows an apparently perfect shape complementarity, burying a total surface of 983 Å². The buried surface area for the variable heavy chain (VH) and light chain (VL) of G1A8 are almost identical (495 Å² versus 488 Å²). The majority of the residues comprising G1A8's epitope are at the N-terminus of FGF19 and within a fragment (SEQ ID NO: 2) consisting of amino acid residues 38-45 of SEQ ID NO: 1, which is situated above the cleft between the VH and VL (FIGS. 7, A and B). This finding is in line with G1A8's designed feature of specifically targeting the N-terminus of FGF19 as described above.

TABLE 1

Crystallographic statistics

| | FGF19-G1A8 Fab |
|---|---|
| Data collection* | |
| Wavelength (Å) | 0.9789 |
| Space group | P2₁2₁2₁ |
| Unit cell dimensions | |
| a, b, c (Å) | 85.0, 104.1, 165.4 |
| α, β, γ (°) | 90.0, 90.0, 90.0 |
| Resolution (Å) | 48.73-2.6 (2.69-2.60) |
| Completeness (%) | 99.7 (99.0) |
| <I/σ(I)> | 24.3 (3.3) |
| CC$_{1/2}$ (%) | 99.7 (95.2) |
| R$_{merge}$ (%) | 1.7(14.5) |
| Multiplicity | 2.0 (2.0) |
| Refinement | |
| Resolution (Å) | 48.7-2.6 (2.66-2.60) |
| No. reflections | 45834 (3207) |
| R$_{work}$/R$_{free}$ (%) | 20.0/25.2 (35.1/40.1) |
| No. atoms | 8740 |
| B factors (Å²) | 63.9 |
| RMS deviation | |
| Bond length (Å) | 0.005 |
| Bond angles (°) | 0.833 |
| Ramachandran statistics | |
| Favored | 96.37% |
| Allowed | 3.63% |
| Outliers | 0 |

*Values in parentheses are for highest shell.

Specifically, the eight residues from positions 38 to 45 of FGF19 engage extensive interactions with all six complementarity-determining-region (CDR) loops from both the VH and VL of G1A8 through a mix of hydrophobic and polar contacts as shown by FIG. 7C and Table 2. The side chain of FGF19 residue Trp38 in the N-terminus is anchored in a hydrophobic pocket formed by Ala33, Ser52, Ser57, Tyr59, Gln102 and Leu104 from HCDR1-3, while Arg45 of FGF19 on the other side engages salt bridge interactions with Glu103 and Asp52 from HCDR3 and LCDR2 respectively (FIG. 7C). FGF19/Trp38Ala mutant showed a reduced binding affinity for G1A8, and mutation of Arg45 into Ala resulted in a complete loss of binding (FIG. 7D), confirming the essentiality of these interactions. FGF19 Arg45 also made additional hydrogen bond interaction with Asn100 from HCDR3 (FIG. 7C). G1A8's parental antibody 31A3 has a Val at this same position, this difference is likely responsible for 31A3's lower affinity than G1A8. (FIG. 2 and FIG. 3A). The G1A8-FGF19 complex structure also revealed the residues 168-172 of the FGF19 at C-terminus are in close proximity with the N-terminus at the interaction interface of FGF19 and G1A8. FGF19's residue Leu169 at the C-terminus in line with the N-terminus forms hydrophobic interaction with Tyr51 and Pro57 from LCDR2. The hydrogen bond between Tyr51 and the backbone carbonyl group of FGF19/Pro167 further stabilizes FGF19 C-terminus interaction. Mutation of Leu169 into Ala results in a reduced binding affinity for antibody due to faster dissociation rate (FIG. 7D).

Contact residues between G1A8 and FGF19

| | HCDR1 | HCDR2 | | HCDR3 | | | | LCDR1 | LCDR2 | | | LCDR3 | |
|---|---|---|---|---|---|---|---|---|---|---|---|---|---|
| G1A8 | A33 | S52 | S57 | N100 | W101 | Q102 | E103 | L104 | Y34 | Y51 | D52 | P57 | W93 | R95 |
| FGF19 | W38 | W38 | W38 | R45 | I42, L44, E81 | W38, I42 | R45 | W38 | P41, R43 | R45, P167, L169 | R45 | L169 | P41 | D40 |

*Contact residues with interatomic distances less than 4 Å are summarized. Underlined residues are involved in hydrogen bond or salt bridge interactions.

The invention claimed is:

1. A monoclonal antibody or an antigen-binding fragment thereof which binds to human fibroblast growth factor 19 (FGF19), comprising:
   (a) a heavy chain variable domain (VH) comprising
   an HCDR1 having the amino acid sequence of SEQ ID NO: 3,
   an HCDR2 having the amino acid sequence of SEQ ID NO: 4,
   an HCDR3 having the amino acid sequence of SEQ ID NO: 19; and
   a light chain variable domain (VL) comprising
   an LCDR1 having the amino acid sequence of SEQ ID NO: 6,
   an LCDR2 having the amino acid sequence of SEQ ID NO: 7,
   an LCDR3 having the amino acid sequence of SEQ ID NO: 14;
   (b) a heavy chain variable domain (VH) comprising
   an HCDR1 having the amino acid sequence of SEQ ID NO: 3,
   an HCDR2 having the amino acid sequence of SEQ ID NO: 4,
   an HCDR3 having the amino acid sequence of SEQ ID NO: 13; and
   a light chain variable domain (VL) comprising
   an LCDR1 having the amino acid sequence of SEQ ID NO: 6,
   an LCDR2 having the amino acid sequence of SEQ ID NO: 7,
   an LCDR3 having the amino acid sequence of SEQ ID NO: 14; or
   (c) a heavy chain variable domain (VH) comprising
   an HCDR1 having the amino acid sequence of SEQ ID NO: 3,
   an HCDR2 having the amino acid sequence of SEQ ID NO: 4,
   an HCDR3 having the amino acid sequence of SEQ ID NO: 5, and
   a light chain variable domain (VL) comprising
   an LCDR1 having the amino acid sequence of SEQ ID NO: 6,
   an LCDR2 having the amino acid sequence of SEQ ID NO: 7,
   an LCDR3 having the amino acid sequence of SEQ ID NO: 8.

2. The antibody or antigen-binding fragment of claim 1, comprising a heavy chain variable domain having at least 95%, 96%, 97%, 98%, 99% or 100% sequence identity to the amino acid sequence of SEQ ID NO: 9, 15, or 20.

3. The antibody or antigen-binding fragment of claim 1, comprising a light chain variable domain having at least 95%, 96%, 97%, 98%, 99% or 100% sequence identity to the amino acid sequence of SEQ ID NO: 10, 16, or 21.

4. The antibody or antigen-binding fragment of claim 1, comprising:
   (a) a heavy chain variable domain having at least 95%, 96%, 97%, 98%, 99% or 100% sequence identity to the amino acid sequence of SEQ ID NO: 9, and a light chain variable domain having at least 95%, 96%, 97%, 98%, 99% or 100% sequence identity to the amino acid sequence of SEQ ID NO: 10;
   (b) a heavy chain variable domain having at least 95%, 96%, 97%, 98%, 99% or 100% sequence identity to the amino acid sequence of SEQ ID NO: 15, and a light chain variable domain having at least 95%, 96%, 97%, 98%, 99% or 100% sequence identity to the amino acid sequence of SEQ ID NO: 16; or
   (c) a heavy chain variable domain having at least 95%, 96%, 97%, 98%, 99% or 100% sequence identity to the amino acid sequence of SEQ ID NO: 20, and a light chain variable domain having at least 95%, 96%, 97%, 98%, 99% or 100% sequence identity to the amino acid sequence of SEQ ID NO: 21.

5. The antibody or antigen-binding fragment of claim 1, comprising:
   (a) a heavy chain variable domain comprising the amino acid sequence of SEQ ID NO: 9, and a light chain variable domain comprising the amino acid sequence of SEQ ID NO: 10;
   (b) a heavy chain variable domain comprising the amino acid sequence of SEQ ID NO: 15, and a light chain variable domain comprising the amino acid sequence of SEQ ID NO: 16; or
   (c) a heavy chain variable domain comprising the amino acid sequence of SEQ ID NO: 20, and a light chain variable domain comprising the amino acid sequence of SEQ ID NO: 21.

6. The antibody or antigen-binding fragment of claim 1, comprising a heavy chain having at least 95%, 96%, 97%, 98%, 99% or 100% sequence identity to the amino acid sequence of SEQ ID NO: 11, 17 or 22.

7. The antibody or antigen-binding fragment of claim 1, comprising a light chain having at least 95%, 96%, 97%, 98%, 99% or 100% sequence identity to the amino acid sequence of SEQ ID NO: 12, 18 or 23.

8. The antibody or antigen-binding fragment of claim 1, comprising:
(a) a heavy chain having at least 95%, 96%, 97%, 98%, 99% or 100% sequence identity to the amino acid sequence of SEQ ID NO: 11, and a light chain having at least 95%, 96%, 97%, 98%, 99% or 100% sequence identity to the amino acid sequence of SEQ ID NO: 12;
(b) a heavy chain having at least 95%, 96%, 97%, 98%, 99% or 100% sequence identity to the amino acid sequence of SEQ ID NO: 17, and a light chain having at least 95%, 96%, 97%, 98%, 99% or 100% sequence identity to the amino acid sequence of SEQ ID NO: 18; or
(c) a heavy chain having at least 95%, 96%, 97%, 98%, 99% or 100% sequence identity to the amino acid sequence of SEQ ID NO: 22, and a light chain having at least 95%, 96%, 97%, 98%, 99% or 100% sequence identity to the amino acid sequence of SEQ ID NO: 23.

9. The antibody or antigen-binding fragment of claim 1, comprising:
(a) a heavy chain comprising the amino acid sequence of SEQ ID NO: 11, and a light chain comprising the amino acid sequence of SEQ ID NO: 12;
(b) a heavy chain comprising the amino acid sequence of SEQ ID NO: 17, and a light chain comprising the amino acid sequence of SEQ ID NO: 18;
(c) a heavy chain comprising the amino acid sequence of SEQ ID NO: 22, and a light chain comprising the amino acid sequence of SEQ ID NO: 23.

10. The antibody or antigen-binding fragment of claim 1, wherein the antigen-binding fragment is a Fab, Fab', F(ab')2, Fv, a single chain Fv (ScFv) or a disulfide-stabilized Fv (dsFv).

11. The antibody or antigen-binding fragment of claim 1, wherein the antibody or antigen-binding fragment thereof has at least one of the following properties: (i) binds to human FGF19 with a KD value of $1\times10^{-9}$ M to $1\times10^{-12}$ M as determined by surface plasmon resonance or a similar technique; (ii) suppresses FGF 19-induced cell proliferation; (iii) does not or minimally affect FGF19-suppressed CYP7A1 expression; and (iv) does not or marginally impair FGF19-maintained bile acid homeostasis.

12. An isolated nucleic acid molecule encoding the antibody or antigen-binding fragment of claim 1.

13. A pharmaceutical composition comprising the antibody or antigen-binding fragment of claim 1, and a pharmaceutically acceptable excipient.

14. A method of treating a cancer, comprising administering to a subject in need thereof a therapeutically effective amount of the antibody or antigen-binding fragment of claim 1, wherein the cancer expresses FGFR4.

15. A method of preventing recurrence of a cancer, comprising administering to a subject in need thereof a therapeutically effective amount of the antibody or antigen-binding fragment of claim 1, wherein the cancer expresses FGFR4.

16. The method of claim 14, wherein the cancer is hepatocellular carcinoma (HCC).

* * * * *